US011739323B2

(12) United States Patent
Hudson et al.

(10) Patent No.: US 11,739,323 B2
(45) Date of Patent: Aug. 29, 2023

(54) MICRO-RNAS AS BIOMARKERS FOR SUBCONCUSSIVE AND CONCUSSIVE INJURY AND THERAPEUTIC APPLICATIONS

(71) Applicant: Temple University—Of The Commonwealth System of Higher Education, Philadelphia, PA (US)

(72) Inventors: Matthew B. Hudson, Philadelphia, PA (US); Dianne Langford, Bala Cynwyd, PA (US); John Jeka, Philadelphia, PA (US); Ryan Tierney, Levittown, PA (US)

(73) Assignee: Temple University-Of The Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 16/001,997

(22) Filed: Jun. 7, 2018

(65) Prior Publication Data

US 2018/0355356 A1  Dec. 13, 2018

Related U.S. Application Data

(60) Provisional application No. 62/516,760, filed on Jun. 8, 2017.

(51) Int. Cl.
| *C12N 15/113* | (2010.01) |
| *C12Q 1/6876* | (2018.01) |
| *A61P 25/00* | (2006.01) |
| *C12Q 1/6883* | (2018.01) |

(52) U.S. Cl.
CPC ............ *C12N 15/113* (2013.01); *A61P 25/00* (2018.01); *C12Q 1/6876* (2013.01); *C12Q 1/6883* (2013.01); *C12N 2310/113* (2013.01); *C12N 2310/141* (2013.01); *C12Q 2600/178* (2013.01)

(58) Field of Classification Search
CPC . A61P 25/00; C12N 15/113; C12N 2310/141; C12Q 2600/178
USPC ............ 435/6.1, 6.11, 91.1, 91.31; 536/23.1, 536/24.5; 514/44 A
See application file for complete search history.

(56) References Cited

U.S. PATENT DOCUMENTS

| 2018/0127828 A1* | 5/2018 | Belli ..................... C12Q 1/6883 |
| 2018/0258483 A1* | 9/2018 | Van Keuren-Jensen ..................... C12Q 1/6883 |
| 2018/0340228 A1* | 11/2018 | Keller ..................... G16H 50/20 |
| 2021/0407677 A1* | 12/2021 | Breiter .................. G16H 10/60 |

FOREIGN PATENT DOCUMENTS

WO  2015134551 A1  9/2015

OTHER PUBLICATIONS

Akao et al., 2007, MicroRNA-143 and -145 in Colon Cancer, DNA and Cell Biol. 26(5):311-320.
Brest et al., 2011, A synonymous variant in IRGM alters a binding site for miR-196 and causes deregulation of IRGM-dependent xenophagy in Crohn's disease, Nature Genetics, 43(3):242-246.
Iorio et al., 2005, MicroRNA Gene Expression Deregulation in Human Breast Cancer, Cancer Research 65(16):7065-7070.
Lawrie et al., 2008, Detection of elevated levels of tumour-associated microRNAs in serum of patients with diffuse large B-cell lymphoma, British Journal of Haematology, 141:672-675.
Marsh et al., 2008, Differential Expression of MicroRNA Species in Human Uterine Leiomyoma versus Normal Myometrium, Fertil Steril. 89(6):1771-1776.
Mitchell et al., 2008, Circulating microRNAs as stable blood-based markers for cancer detection, PNAS, 105(30):10513-10518.
Small et al., 2011, Pervasive roles of microRNAs in cardiovascular biology, Nature, 469(7330):336-342.
Yang et al., 2008, MicroRNA Expression Profiling in Human Ovarian Cancer: miR-214 Induces Cell Survival and Cisplatin Resistance by Targeting PTEN, Cancer Research, 8(2):425-433.
Yang et al., 2008, MicroRNA Microarray Identifies Let-7i as a Novel Biomarker and Therapeutic Target in Human Epithelial Ovarian Cancer, Cancer Research, 68(4):1037-10314.

* cited by examiner

*Primary Examiner* — Jane J Zara
(74) *Attorney, Agent, or Firm* — Riverside Law LLP

(57) ABSTRACT

The invention includes compositions and methods useful for the diagnosis and treatment of head or brain injury in a subject in need thereof, based upon the expression level of at least one miRNA that is associated with head or brain injury.

2 Claims, 3 Drawing Sheets

| Ortholog of target gene | Protein | Representative transcript | Gene name | 3P-seq tags + 5 | Total sites | 8mer sites | 7mer m8 sites | 7mer A1 sites | 6mer sites | Cumulative weighted context++ | Total context++ score |
|---|---|---|---|---|---|---|---|---|---|---|---|
| LIMS1 | PINCH | ENST00000393310.1 | LIM and senescent cell | 68 | 3 | 0 | 0 | 0 | 3 | -0.02 | -0.12 |
| CLDN01 | | ENST00000341181.6 | claudin domain | 24 | 1 | 0 | 1 | 0 | 0 | -0.04 | -0.13 |
| CLDN12 | Claudin 12 | ENST00000287916.4 | claudin 12 | 267 | 2 | 1 | 1 | 0 | 0 | -0.34 | -0.34 |
| OCLN | Occludin | ENST00000355237.2 | occludin | 5 | 1 | 0 | 0 | 1 | 4 | -0.02 | -0.02 |
| TJP1 | Tight Junction Protein 1 (ZO-1) | ENST00000346128.6 | tight junction protein 1 | 140 | 2 | 0 | 2 | 0 | 0 | -0.01 | -0.06 |
| F11R | JAM A | ENST00000368026.5 | F11 receptor | 2844 | 1 | 0 | 0 | 1 | 1 | -0.01 | -0.03 |
| ATG12 | | ENST00000509945.2 | autophagy related 12 | 1822 | 3 | 0 | 1 | 2 | 0 | -0.15 | -0.33 |
| MAP1LC3B | LC3B | ENST00000268607.5 | microtubule-associated protein 1 light chain 3 | 18 | 2 | 0 | 1 | 0 | 1 | -0.02 | -0.04 |
| ATG13 | | ENST00000395513.4 | autophagy related 13 | 834 | 1 | 0 | 1 | 0 | 0 | 0 | -0.02 |
| ATG14 | | ENST00000247178.5 | autophagy related 14 | 25 | 2 | 0 | 0 | 0 | 2 | 0 | -0.01 |
| CDK2 | | ENST00000266970.4 | cyclin-dependent kinase 2 | 6789 | 1 | 0 | 1 | 0 | 1 | -0.23 | -0.23 |
| MAPK8 | JNK1 | ENST00000374182.3 | mitogen-activated | 227 | 2 | 1 | 0 | 0 | 3 | -0.12 | -0.19 |
| CDK13 | | ENST00000181839.4 | cyclin-dependent kinase | 32 | 1 | 0 | 0 | 1 | 3 | -0.1 | -0.1 |
| SPP1 | Osteopontin | ENST00000237623.7 | secreted phosphoprotein | 15 | 2 | 0 | 0 | 1 | 0 | -0.09 | -0.09 |
| CDK8 | | ENST00000381527.3 | cyclin-dependent kinase 8 | 280 | 1 | 0 | 0 | 1 | 1 | -0.07 | -0.07 |
| MAPK3 | | ENST00000403394.1 | mitogen-activated | 271 | 1 | 0 | 1 | 0 | 0 | -0.06 | -0.06 |
| CDK15 | | ENST00000450471.2 | cyclin-dependent kinase | 7 | 1 | 0 | 0 | 1 | 0 | -0.06 | -0.06 |
| CDK6 | | ENST00000265734.4 | cyclin-dependent kinase 6 | 1116 | 2 | 1 | 1 | 0 | 6 | -0.05 | -0.05 |
| CDK12 | | ENST00000447079.4 | cyclin-dependent kinase | 748 | 1 | 1 | 0 | 0 | 3 | -0.03 | -0.03 |
| CDK17 | | ENST00000543119.2 | cyclin-dependent kinase | 475 | 1 | 1 | 0 | 0 | 2 | -0.02 | -0.02 |
| ITGA1 | itbeta-1 | ENST00000282588.6 | integrin, alpha 1 | 400 | 1 | 0 | 0 | 1 | 3 | -0.02 | -0.02 |
| MAPK14 | | ENST00000229795.3 | mitogen-activated | 1191 | 1 | 0 | 0 | 1 | 2 | -0.01 | -0.01 |
| MAPK1 | | ENST00000215832.5 | mitogen-activated | 630 | 2 | 1 | 0 | 1 | 0 | 0 | -0.06 |
| MAPK13 | | ENST00000211287.4 | mitogen-activated | 499 | 1 | 0 | 1 | 0 | 0 | -0.02 | -0.02 |
| GSK3B | | ENST00000264235.8 | glycogen synthase kinase | 498 | 1 | 0 | 1 | 0 | 2 | -0.01 | -0.02 |
| ITGB8 | | ENST00000222573.4 | integrin, beta 8 | 17 | 1 | 0 | 1 | 0 | 2 | -0.09 | -0.09 |
| ITGA7 | | ENST00000553804.1 | integrin, alpha 7 | 100 | 1 | 0 | 1 | 0 | 1 | -0.05 | -0.05 |
| ITGA8 | | ENST00000378076.3 | integrin, alpha 8 | 7 | 2 | 0 | 1 | 1 | 0 | -0.03 | -0.03 |
| ITGB6 | | ENST00000283249.2 | integrin, beta 6 | 5 | 1 | 0 | 0 | 1 | 0 | -0.03 | -0.03 |
| ITGA2 | | ENST00000296585.5 | integrin, alpha 2 (CD49B, alpha 2 subunit of VLA-2 | 50 | 1 | 1 | 0 | 0 | 2 | -0.03 | -0.03 |
| ITGB3 | | ENST00000559488.1 | integrin, beta 3 (platelet glycoprotein IIIa, antigen | 176 | 1 | 0 | 1 | 0 | 0 | -0.02 | -0.02 |
| STUB1 | | ENST00000219548.4 | STIP1 homology and U-box containing protein 1, | 1094 | 1 | 0 | 0 | 1 | 0 | -0.13 | -0.13 |

Figure 1

MICRO-RNAS AS BIOMARKERS FOR SUBCONCUSSIVE AND CONCUSSIVE INJURY AND THERAPEUTIC APPLICATIONS

CROSS REFERENCE TO RELATED APPLICATIONS

This application claims priority to U.S. Provisional Application No. 62/516,760, filed Jun. 8, 2017 which is hereby incorporated by reference herein in its entirety.

BACKGROUND OF THE INVENTION

Currently, severity of head impact is often assessed through subjective means allowing for many head injuries to go undiagnosed. Furthermore, although biomarkers have been identified to indicate brain injury, these biomarkers lack the sensitivity and specificity to be a truly effective diagnostic or prognostic tool. In fact, low-level impact hits that have recently been shown to impact memory may not even be detectable by current technologies.

Recent research has shown that small circulating molecules termed exosomes contain cargo including microRNAs that may be indicative of pathological events and signaling occurring in the tissue from which they were released. MicroRNAs (miRNAs) are a family of endogenous, small (approximately 22 nucleotides in length), non-coding, functional RNAs, and these sequences control gene expression either by translational repression or degradation of messenger RNA transcripts after targeting the 3'-untranslated region (3'-UTR). Increasing evidence suggests that miRNAs are pivotal regulators of development and cellular homeostasis through their control of diverse biologic processes. Numerous studies have shown that aberrant miRNA expression is associated with several human diseases such as cancer, cardiovascular disorders, and inflammatory diseases as well as with gynecologic pathology (Iorio et al., 2005, Cancer Res, 65: 7065-7070; Akao et al., 2007, DNA Cell Biol, 26: 311-320; Yang et al., 2008, Cancer Res, 68: 425-433; Small et al., 2011, Nature, 469: 336-342; Brest et al., 2011, Nat Genet, 43: 242-245; Yang et al., 2008, Cancer Res, 68: 10307-10314; Marsh et al., 2008, Fertil Steril, 89: 1771-1776). Recently, the presence of circulating miRNAs was demonstrated in the blood (Mitchell et al., 2008, Proc Natl Acad Sci USA, 105: 10513-10518). Since their first description as potential diagnostic biomarkers for diffuse large B-cell lymphoma (Lawrie et al., 2008, Br J Haematol, 141: 672-675), it has been demonstrated that circulating miRNAs may be used as noninvasive biomarkers for other conditions.

Additionally, there are currently no therapeutic options available to reverse the effects of head injury. However, recent evidence indicates that microRNAs can be used therapeutically to alter the level of proteins involved in pathological processes.

Development of both new noninvasive diagnostic markers for head impacts and therapeutic options is crucial for proper treatment and management of the disease. The present invention addresses this unmet need in the art.

BRIEF DESCRIPTION OF THE DRAWINGS

The following detailed description of exemplary embodiments of the invention will be better understood when read in conjunction with the appended drawings, for the purpose of illustrating the invention. It should be understood that the invention is not limited to the precise arrangements and instrumentalities of the embodiments shown in the drawings.

FIG. 1 provides a table of predicted targets of miR-7844-5p involved in head injury.

DETAILED DESCRIPTION

Figure 2:
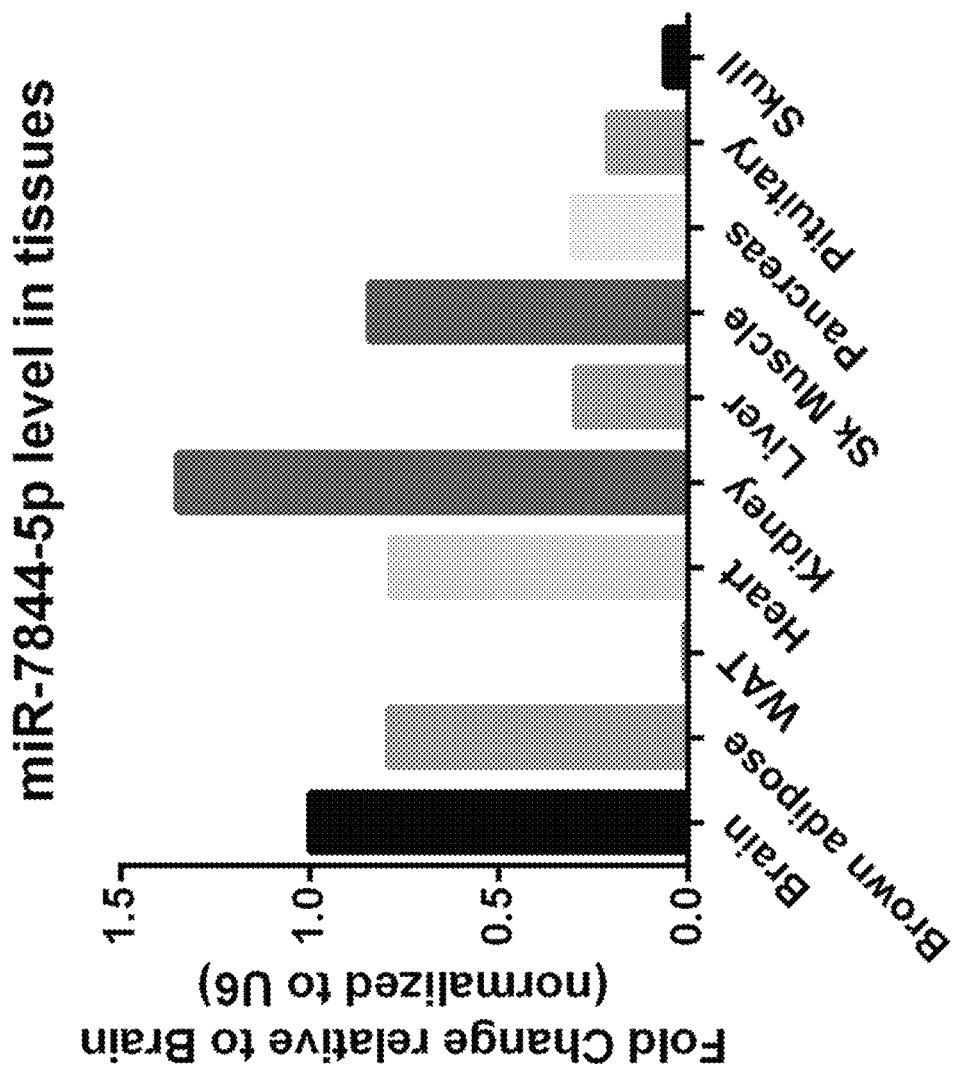
FIG. 2 depicts experimental results demonstrating the miR-7844-5p levels in various tissues.

The present invention relates to the discovery that the microRNA (miR) content is altered in circulating exosomes of subjects who have experienced repetitive low levels of head impact. Further, the invention is partly based on the discovery that miR-7844-5p has been identified as a therapeutic agent for treatment of concussive or subconcussive head injury. Thus, in one embodiment, the present invention provides markers for the diagnosis of concussive or subconcussive head injury. Generally, the methods of the invention find use in diagnosing concussive or subconcussive head injury by detecting the levels of at least one miRNA associated with concussive or subconcussive head injury markers in a sample of a subject. In one embodiment, the sample contains circulating exosomes.

In one embodiment, miRNAs that are increased or decreased in circulating exosomes of subjects who have experienced repetitive low levels of head impact relative to control subjects are considered to be markers or biomarkers for concussive or subconcussive head injury. In one embodiment, the markers of the invention include one or more of miR-92b-5p, miR-423-5p, miR-24-3p, miR-7844-5p, miR-144-5p, miR-221-5p, and miR-22-3p. In one embodiment, one or more of miR-92b-5p, miR-423-5p and miR-24-3p is increased in abundance in circulating exosomes of subjects who have experienced repetitive low levels of head impact relative to control subjects. In one embodiment, one or more of miR-7844-5p, miR-144-5p, miR-221-5p, and miR-22-3p is decreased in abundance in circulating exosomes of subjects who have experienced repetitive low levels of head impact relative to control subjects.

In one embodiment, the invention relates to pharmaceutical compositions and methods for treating head or brain injury. In one embodiment, a head or brain injury is a concussive or subconcussive head or brain injury. In one embodiment, the invention relates to pharmaceutical compositions and the methods for treating brain injury due to HIV, Alzheimers, Epilepsy, stroke, and inflammatory diseases of the brain. In one embodiment, the method of treating head or brain injury in a subject comprises diagnosing a subject as having a head or brain injury and administering a pharmaceutical composition to the subject in need thereof.

In one embodiment, a composition for treating head or brain injury increases the level or activity of at least one of miR-7844-5p, miR-144-5p, miR-221-5p, and miR-22-3p in the subject. In one embodiment, a composition for treating head or brain injury decreases the level or activity of at least one of miR-92b-5p, miR-423-5p and miR-24-3p in the subject. In one embodiment, the composition comprises miR-7844-5p.

In one embodiment, the invention relates to kits for use in a method of diagnosing head or brain injury.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

"Antisense," as used herein, refers to a nucleic acid sequence which is complementary to a target sequence, such as, by way of example, complementary to a target miRNA sequence, including, but not limited to, a mature target miRNA sequence, or a sub-sequence thereof. Typically, an antisense sequence is fully complementary to the target sequence across the full length of the antisense nucleic acid sequence.

The term "body fluid" or "bodily fluid" as used herein refers to any fluid from the body of an animal. Examples of body fluids include, but are not limited to, plasma, serum, blood, lymphatic fluid, cerebrospinal fluid, synovial fluid, urine, saliva, mucous, phlegm and sputum. A body fluid sample may be collected by any suitable method. The body fluid sample may be used immediately or may be stored for later use. Any suitable storage method known in the art may be used to store the body fluid sample: for example, the sample may be frozen at about −20° C. to about −70° C. Suitable body fluids are acellular fluids. "Acellular" fluids include body fluid samples in which cells are absent or are present in such low amounts that the miRNA level determined reflects its level in the liquid portion of the sample, rather than in the cellular portion. Such acellular body fluids are generally produced by processing a cell-containing body fluid by, for example, centrifugation or filtration, to remove the cells. Typically, an acellular body fluid contains no intact cells however, some may contain cell fragments or cellular debris. Examples of acellular fluids include plasma or serum, or body fluids from which cells have been removed.

The term "clinical factors" as used herein, refers to any data that a medical practitioner may consider in determining a diagnosis of disease. Such factors include, but are not limited to, the patient's medical history, a physical examination of the patient, results of a CT scan, complete blood count, analysis of the activity of enzymes, examination of cells, cytogenetics, and immunophenotyping of blood cells.

"Complementary" as used herein refers to the broad concept of subunit sequence complementarity between two nucleic acids. When a nucleotide position in both of the molecules is occupied by nucleotides normally capable of base pairing with each other, then the nucleic acids are considered to be complementary to each other at this position. Thus, two nucleic acids are substantially complementary to each other when at least about 50%, at least about 60% or at least about 80% of corresponding positions in each of the molecules are occupied by nucleotides which normally base pair with each other (e.g., A:T and G:C nucleotide pairs).

As used herein, the term "diagnosis" means detecting a disease or disorder or determining the stage or degree of a disease or disorder. Usually, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease; i.e. there may be differential diagnoses that can be inferred from a diagnostic factor or symptom. Likewise, there may be instances where a factor or symptom that is indicative of a particular disease is present in an individual that does not have the particular disease. The diagnostic methods may be used independently, or in combination with other diagnosing and/or staging methods known in the medical art for a particular disease or disorder.

As used herein, the phrase "difference of the level" refers to differences in the quantity of a particular marker, such as a nucleic acid or a protein, in a sample as compared to a control or reference level. For example, the quantity of a particular marker may be present at an elevated amount or at a decreased amount in samples of patients with a disease compared to a reference level. In one embodiment, a "difference of a level" may be a difference between the quantity of a particular marker present in a sample as compared to a control of at least about 1%, at least about 2%, at least about 3%, at least about 5%, at least about 10%, at least about 15%, at least about 20%, at least about 25%, at least about 30%, at least about 35%, at least about 40%, at least about 50%, at least about 60%, at least about 75%, at least about 80% or more. In one embodiment, a "difference of a level" may be a difference between the quantity of a particular marker present in a sample as compared to a control of at least about 1.1 fold, at least 1.2 fold, at least 1.4 fold, at least 1.6 fold, at least 1.8 fold, at least 2 fold, at least 3 fold, at least 4 fold, at least 5 fold, at least 6 fold, at least 7 fold, at least 8 fold, at least 9 fold, at least 10 fold or more. In one embodiment, a "difference of a level" may be a statistically significant difference between the quantity of a marker present in a sample as compared to a control. For example, a difference may be statistically significant if the measured level of the marker falls outside of about 1.0 standard deviations, about 1.5 standard deviations, about 2.0 standard deviations, or about 2.5 stand deviations of the mean of any control or reference group.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

The term "control or reference standard" describes a material comprising none, or a normal, low, or high level of one of more of the marker (or biomarker) expression products of one or more the markers (or biomarkers) of the invention, such that the control or reference standard may serve as a comparator against which a sample can be compared.

The terms "dysregulated" and "dysregulation" as used herein describes a decreased (down-regulated) or increased (up-regulated) level of expression of a miRNA present and detected in a sample obtained from subject as compared to the level of expression of that miRNA in a comparator sample, such as a comparator sample obtained from one or more normal, not-at-risk subjects, or from the same subject at a different time point. In some instances, the level of miRNA expression is compared with an average value obtained from more than one not-at-risk individuals. In other instances, the level of miRNA expression is compared with a miRNA level assessed in a sample obtained from one normal, not-at-risk subject.

By the phrase "determining the level of marker (or biomarker) expression" is meant an assessment of the degree of expression of a marker in a sample at the nucleic acid or protein level, using technology available to the skilled artisan to detect a sufficient portion of any marker expression product.

The terms "determining," "measuring," "assessing," and "assaying" are used interchangeably and include both quantitative and qualitative measurement, and include determining if a characteristic, trait, or feature is present or not. Assessing may be relative or absolute. "Assessing the presence of" includes determining the amount of something present, as well as determining whether it is present or absent.

"Differentially increased expression" or "up regulation" refers to expression levels which are at least 10% or more, for example, 20%, 30%, 40%, or 50%, 60%, 70%, 80%, 90% higher or more, and/or 1.1 fold, 1.2 fold, 1.4 fold, 1.6 fold, 1.8 fold, 2.0 fold, 3.0 fold, 4.0 fold higher or more, and any and all whole or partial increments there between than a comparator.

"Differentially decreased expression" or "down regulation" refers to expression levels which are at least 10% or more, for example, 20%, 30%, 40%, or 50%, 60%, 70%, 80%, 90% lower or less, and/or 4.0 fold, 3.0 fold, 2.0 fold, 1.8 fold, 1.6 fold, 1.4 fold, 1.2 fold, 1.1 fold or less lower, and any and all whole or partial increments there between than a comparator.

As used herein "endogenous" refers to any material from or produced inside an organism, cell, tissue or system.

The term "expression" as used herein is defined as the transcription and/or translation of a particular nucleotide sequence.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology.

As used herein, "homology" is used synonymously with "identity."

"Inhibitors" and "activators" of the markers are used to refer to activating or inhibitory molecules of identified head or brain injury markers. Inhibitors are compounds that, e.g., bind to, partially or totally block activity, decrease, prevent, delay activation, inactivate, desensitize, or down regulate the level, activity or expression of head or brain injury markers. "Activators" are compounds that increase, open, activate, facilitate, enhance activation, sensitize, agonize, or up regulate the level, activity or expression of head or brain injury markers, e.g., agonists. Inhibitors or activators also include genetically modified versions of head or brain injury markers, e.g., versions with altered activity, as well as naturally occurring and synthetic ligands, antagonists, agonists, antibodies, peptides, cyclic peptides, nucleic acids, antisense molecules, ribozymes, RNAi, microRNA, and siRNA molecules, small organic molecules and the like.

As used herein, an "instructional material" includes a publication, a recording, a diagram, or any other medium of expression which can be used to communicate the usefulness of a compound, composition, vector, method or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

As used herein, "isolated" means altered or removed from the natural state through the actions, directly or indirectly, of a human being. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's clinical parameters.

As used herein, "microRNA," "miRNA," or "miR" describes small non-coding RNA molecules, generally about 15 to about 50 nucleotides in length, in one embodiment about 17-23 nucleotides in length, which can play a role in regulating gene expression through, for example, a process termed RNA interference (RNAi). RNAi describes a phenomenon whereby the presence of an RNA sequence that is complementary or antisense to a sequence in a target gene messenger RNA (mRNA) results in inhibition of expression of the target gene. miRNAs are processed from hairpin precursors of about 70 or more nucleotides (pre-miRNA) which are derived from primary transcripts (pri-miRNA)

through sequential cleavage by RNAse III enzymes. miR-Base is a comprehensive microRNA database located at www.mirbase.org, incorporated by reference herein in its entirety for all purposes.

"Naturally occurring" as used herein describes a composition that can be found in nature as distinct from being artificially produced. For example, a nucleotide sequence present in an organism, which can be isolated from a source in nature and which has not been intentionally modified by a person, is naturally occurring.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand." Sequences on the DNA strand which are located 5' to a reference point on the DNA are referred to as "upstream sequences." Sequences on the DNA strand which are 3' to a reference point on the DNA are referred to as "downstream sequences."

As used herein, "polynucleotide" includes cDNA, RNA, DNA/RNA hybrid, anti-sense RNA, siRNA, miRNA, genomic DNA, synthetic forms, and mixed polymers, both sense and antisense strands, and may be chemically or biochemically modified to contain non-natural or derivatized, synthetic, or semi-synthetic nucleotide bases. Also, included within the scope of the invention are alterations of a wild type or synthetic gene, including but not limited to deletion, insertion, substitution of one or more nucleotides, or fusion to other polynucleotide sequences.

As used herein, a "primer" for amplification is an oligonucleotide that specifically anneals to a target or marker nucleotide sequence. The 3' nucleotide of the primer should be identical to the target or marker sequence at a corresponding nucleotide position for optimal primer extension by a polymerase. As used herein, a "forward primer" is a primer that anneals to the anti-sense strand of double stranded DNA (dsDNA). A "reverse primer" anneals to the sense-strand of dsDNA.

The term "recombinant DNA" as used herein is defined as DNA produced by joining pieces of DNA from different sources.

A "reference level" of a marker means a level of the marker that is indicative of a particular disease state, phenotype, or lack thereof, as well as combinations of disease states, phenotypes, or lack thereof. A "positive" reference level of a marker means a level that is indicative of a particular disease state or phenotype. A "negative" reference level of a marker means a level that is indicative of a lack of a particular disease state or phenotype.

"Sample" or "biological sample" as used herein means a biological material isolated from an individual. The biological sample may contain any biological material suitable for detecting the desired markers, and may comprise cellular and/or non-cellular material obtained from the individual.

"Standard control value" as used herein refers to a predetermined amount of a particular protein or nucleic acid that is detectable in a biological sample. The standard control value is suitable for the use of a method of the present invention, in order for comparing the amount of a protein or nucleic acid of interest that is present in a biological sample. An established sample serving as a standard control provides an average amount of the protein or nucleic acid of interest in the biological sample that is typical for an average, healthy person of reasonably matched background, e.g., gender, age, ethnicity, and medical history. A standard control value may vary depending on the protein or nucleic acid of interest and the nature of the sample (e.g., serum).

The terms "subject," "patient," "individual," and the like are used interchangeably herein, and refer to any animal, or cells thereof whether in vitro or in situ, amenable to the methods described herein. In certain non-limiting embodiments, the patient, subject or individual is a human.

The terms "underexpress", "underexpression", "underexpressed", or "down-regulated" interchangeably refer to a protein or nucleic acid that is transcribed or translated at a detectably lower level in a biological sample from a subject with a head or brain injury, in comparison to a biological sample from a subject without a head or brain injury. The term includes underexpression due to transcription, post transcriptional processing, translation, post-translational processing, cellular localization (e.g., organelle, cytoplasm, nucleus, cell surface, exosome), and RNA and protein stability, as compared to a control. Underexpression can be detected using conventional techniques for detecting mRNA (i.e., Q-PCR, RT-PCR, PCR, hybridization) or proteins (i.e., ELISA, immunohistochemical techniques). Underexpression can be 10%, 20%, 30%, 40%, 50%, 60%, 70%, 80%, 90% or less in comparison to a control. In certain instances, underexpression is 1-, 2-, 3-, 4-, 5-, 6-, 7-, 8-, 9-, 10-fold or more lower levels of transcription or translation in comparison to a control.

The terms "overexpress", "overexpression", "overexpressed", or "up-regulated" interchangeably refer to a protein or nucleic acid (RNA) that is transcribed or translated at a detectably greater level, usually in a biological sample from a subject with a head or brain injury, in comparison to a biological sample from a subject without a head or brain injury. The term includes overexpression due to transcription, post transcriptional processing, translation, post-translational processing, cellular localization (e.g., organelle, cytoplasm, nucleus, cell surface, exosome), and RNA and protein stability, as compared to a cell from a subject without a head or brain injury. Overexpression can be detected using conventional techniques for detecting mRNA (i.e., Q-PCR, RT-PCR, PCR, hybridization) or proteins (i.e., ELISA, immunohistochemical techniques). Overexpression can be 10%, 20%, 30%, 40%, 50%, 60%, 70%, 80%, 90% or more in comparison to a sample from a subject without a head or brain injury. In certain instances, overexpression is 1-, 2-, 3-, 4-, 5-, 6-, 7-, 8-, 9-, 10-fold, or more higher levels of transcription or translation in comparison to a sample from a subject without a head or brain injury.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

In one aspect, the present invention relates to the discovery of a link between alterations in circulating miRNA (miR) levels and head or brain injury. In various embodiments a head or brain injury is a concussive or subconcussive head or brain injury. In one embodiment, a head or brain injury is due to HIV, Alzheimers, Epilepsy, stroke, or an inflammatory disease of the brain. In some embodiments, the level of circulating miRs, alone or in combination with additional serum markers, are used to detect head or brain injury. In one embodiment, the miRs are at least one of: miR-92b-5p, miR-423-5p, miR-24-3p, miR-7844-5p, miR-144-5p, miR-221-5p, and miR-22-3p, and any combination thereof.

In some embodiments, one or more miR, pre-miR, miR mimic, anti-miR or miR modulator are provided as therapeutic agents for the treatment of head or brain injury.

Methods of Diagnosing and Treating Head or Brain Injury

In one aspect, the methods generally provide for the detection, measuring, and comparison of a pattern of miR in circulating exosomes in a patient sample. In the context of head or brain injury, access to the injured or diseased cells is not an option. The present methods overcome problems of head or brain injury diagnosis by determining the levels of miRs in the exosomes of patients with a head injury. An alteration (i.e., an increase or decrease) in the level of a miR in the sample obtained from the subject, relative to the level of a corresponding miR in a control sample, is indicative of the presence of head or brain injury in the subject. In one embodiment, the level of at least one miR in the test sample is greater than the level of the corresponding miR in the control sample. In another embodiment, the level of at least one miR in the test sample is less than the level of the corresponding miR in the control sample.

Additional diagnostic markers may be combined with the circulating exosomal miR level to construct models for predicting the presence or absence or stage of a disease. For example, clinical factors of relevance to the diagnosis of head or brain injury, include, but are not limited to, the patient's medical history, a physical examination, results of a CT scan, and other markers.

Generally, the methods of this invention find use in diagnosing head or brain injury by detecting the expression levels of markers, which are increased or decreased in exosomes from a patient. In one embodiment, the exosomes are from blood or serum from a patient. The markers of the present invention can be used alone or in combination for the diagnosis of head or brain injury.

In one embodiment, the methods of the present invention find use in treating a patient suffering from head or brain injury. By detecting the expression levels of markers found herein, the appropriate treatment can be assigned to a patient suffering from a head or brain injury. These treatments can include, but are not limited to administration of a therapeutic composition for increasing or decreasing the level or activity of one or more microRNA associated with head or brain injury. These treatments can include, but are not limited to administration of a therapeutic composition for increasing or decreasing the level or activity of one or more target of a microRNA associated with head or brain injury.

In one embodiment, the treatment comprises administration of a composition comprising an activator of one or more of miR-7844-p5 to a subject identified as having a head or brain injury. In one embodiment, the treatment comprises administration of a composition comprising miR-7844-p5, pre-miR-7844-p5 or a mimic thereof to a subject identified as having a head or brain injury. In one embodiment, the treatment comprises administration of a composition comprising an activator or inhibitor of one or more of LIMS1, CLDND1, CLDN12, OCLN, TJP1, F11R, ATG13, ATG14, CDK2, MAPK8, CDK13, SPP1, CDK8, MAPK3, CKD15, CDK6, CDK12, CDK17, ITGA1, MAPK14, MAPK1, MAPK13, GSK3B, ITGB8, ITGA7, ITGA8, ITGB6, ITGA2, ITGB3 and STUB1 to a subject identified as having a head or brain injury.

Diagnostic kits comprising one or more markers for use are provided herein. Also provided by the invention are methods for identifying compounds that are able to prevent or treat head or brain injury by modulating the expression level or activity of markers found in any one of the identified gene subsets. Therapeutic methods are provided, wherein head or brain injury is treated using an agent that targets the markers of the invention.

In some embodiments, a miR associated with head or brain injury is reduced, or present at a lower than normal level in the exosomes of a subject with an injury. Thus, the invention relates to compositions and methods useful for the diagnosis, assessment, and characterization of head or brain injury in a subject in need thereof, based upon the reduced level of at least one miR that is associated with head or brain injury. Accordingly, in one embodiment, the invention provides a method of treating head or brain injury by targeting the miRs that are reduced in order to increase the expression of these miRs. In one embodiment, the invention provides a method of treating head or brain injury by administering to the subject a composition comprising one or more of the miRs that are reduced in order to increase the level of these miRs.

In some embodiments, a miR associated with head or brain injury is increased, or present at a higher than normal level in the exosomes of a subject with an injury. Thus, the invention relates to compositions and methods useful for the diagnosis, assessment, and characterization of head or brain injury in a subject in need thereof, based upon identifying an increased level of at least one miR that is associated with head or brain injury. Accordingly, the invention provides a method of treating head or brain injury by targeting the miRs that are increased in order to reduce the level or expression of these miRs.

In one embodiment, the markers of the invention include one or more of miR-7844-5p, miR-144-5p, miR-221-5p, miR-22-3p, miR-92b-5p, miR-423-5p, and miR-24-3p. MicroRNAs that have been identified as being reduced in head or brain injury include miR-7844-5p, miR-144-5p, miR-221-5p, and miR-22-3p miRNAs. MicroRNAs that have been identified as being increased in head or brain injury include miR-92b-5p, miR-423-5p, and miR-24-3p miRNAs.

Sample Preparation

Test samples of acellular body fluid or cell-containing samples may be obtained from an individual or patient. Methods of obtaining test samples are well-known to those of skill in the art and include, but are not limited to aspirations or drawing of blood or other fluids. Samples may include, but are not limited to, whole blood, serum, plasma, saliva, cerebrospinal fluid (CSF), pericardial fluid, pleural fluid, urine, and eye fluid. In some embodiments in which the test sample contains cells, the cells may be removed from the liquid portion of the sample by methods known in the art (e.g., centrifugation) to yield acellular body fluid. In suitable embodiments, serum or plasma are used as the acellular body fluid sample. Plasma and serum can be prepared from whole blood using suitable methods well-known in the art. In these embodiments, data may be normalized by volume of acellular body fluid.

Variability in sample preparation of cell-containing samples can be corrected by normalizing the data by, for example, protein content or cell number. In certain embodiments, the sample may be normalized relative to the total protein content in the sample. Total protein content in the sample can be determined using standard procedures, including, without limitation, Bradford assay and the Lowry method. In other embodiments, the sample may be normalized relative to cell number.

Any method known in the art for isolating and purifying exosomes is appropriate for use in the method of the invention. Various methods for isolation of exosomes from biological fluids have been developed. They include, but are not limited to, centrifugation, chromatography, filtration, polymer-based precipitation and immunological separation (e.g. immunobeads).

Any method known in the art for isolating and purifying exosomal miR is appropriate for use in the method of the invention. Various methods for isolation of miR content from exosomes have been developed. They include, but are not limited to, phenol chloroform extraction or the use of a kit for extraction of miR from exosomes.

Assays

The present invention relates to the discovery that the level of particular miRs in exosomes is associated with head or brain injury. In various embodiments, the invention relates to a screening assay of a subject to determine the level of at least one miR associated with head or brain injury in the subject. The present invention provides methods of assessing level of at least one miR associated with head or brain injury, as well as methods of diagnosing a subject as having head or brain injury based upon the level of expression of at least one miR associated with head or brain injury. In some embodiments, the diagnostic assays described herein are in vitro assays.

In one embodiment, the method of the invention is a diagnostic assay for assessing the presence of a head or brain injury in a subject in need thereof, by determining whether the level of at least one miR associated with head or brain injury is decreased in a biological sample obtained from the subject. In various embodiments, to determine whether the level of the at least one miR associated with head or brain injury is decreased in a biological sample obtained from the subject, the level of the at least one miR is compared with the level of at least one comparator control, such as a positive control, a negative control, a normal control, a wild-type control, a historical control, a historical norm, or the level of another reference molecule in the biological sample. In some embodiments, the diagnostic assay of the invention is an in vitro assay. In other embodiments, the diagnostic assay of the invention is an in vivo assay. The miR identified by the assay can be a miR that is associated with head or brain injury. In some embodiments, the miR is at least one of miR-7844-5p, miR-144-5p, miR-221-5p, and miR-22-3p. In various embodiments of the invention, the at least one miR associated with head or brain injury is at least two miRs, at least three miRs or at least four miRs. The results of the diagnostic assay can be used alone, or in combination with other information from the subject, or other information from the biological sample obtained from the subject.

In various embodiments of the assays of the invention, the level of the at least one miR associated with head or brain injury is determined to be decreased when the level of the at least one miR is decreased by at least 5%, at least 10%, by at least 20%, by at least 30%, by at least 40%, by at least 50%, by at least 60%, by at least 70%, by at least 80%, by at least 90%, by at least 100%, by at least 125%, by at least 150%, by at least 175%, by at least 200%, by at least 250%, by at least 300%, by at least 400%, by at least 500%, by at least 600%, by at least 700%, by at least 800%, by at least 900%, by at least 1000%, by at least 1500%, by at least 2000%, or by at least 5000%, when compared with a comparator control.

In various embodiments of the assays of the invention, the level of the at least one miR associated with head or brain injury is determined to be decreased when the level of the at least one miR is decreased by at least about 1.1 fold, at least 1.2 fold, at least 1.4 fold, at least 1.6 fold, at least 1.8 fold, at least 2 fold, at least 3 fold, at least 4 fold, at least 5 fold, at least 6 fold, at least 7 fold, at least 8 fold, at least 9 fold, at least 10 fold or more, when compared with a comparator control.

In one embodiment, the method of the invention is a diagnostic assay for assessing the presence of a head or brain injury in a subject in need thereof, by determining whether the level of at least one miR associated with head or brain injury is increased in a biological sample obtained from the subject. In various embodiments, to determine whether the level of the at least one miR associated with head or brain injury is increased in a biological sample obtained from the subject, the level of the at least one miR is compared with the level of at least one comparator control, such as a positive control, a negative control, a normal control, a wild-type control, a historical control, a historical norm, or the level of another reference molecule in the biological sample. In some embodiments, the diagnostic assay of the invention is an in vitro assay. In other embodiments, the diagnostic assay of the invention is an in vivo assay. The miR identified by the assay can be a miR that is associated with head or brain injury. In some embodiments, the miR is at least one of miR-92b-5p, miR-423-5p, and miR-24-3p miRNAs. In various embodiments of the invention, the at least one miR associated with head or brain injury is at least two miRs, or at least three miRs. The results of the diagnostic assay can be used alone, or in combination with other information from the subject, or other information from the biological sample obtained from the subject.

In various embodiments of the assays of the invention, the level of the at least one miR associated with head or brain injury is determined to be increased when the level of the at least one miR is increased by at least 5%, at least 10%, by at least 20%, by at least 30%, by at least 40%, by at least 50%, by at least 60%, by at least 70%, by at least 80%, by at least 90%, by at least 100%, by at least 125%, by at least 150%, by at least 175%, by at least 200%, by at least 250%, by at least 300%, by at least 400%, by at least 500%, by at least 600%, by at least 700%, by at least 800%, by at least 900%, by at least 1000%, by at least 1500%, by at least 2000%, or by at least 5000%, when compared with a comparator control.

In various embodiments of the assays of the invention, the level of the at least one miR associated with head or brain injury is determined to be increased when the level of the at least one miR is increased by at least about 1.1 fold, at least 1.2 fold, at least 1.4 fold, at least 1.6 fold, at least 1.8 fold, at least 2 fold, at least 3 fold, at least 4 fold, at least 5 fold, at least 6 fold, at least 7 fold, at least 8 fold, at least 9 fold, at least 10 fold or more, when compared with a comparator control.

In the assay methods of the invention, a test biological sample from a subject is assessed for the level of at least one miR associated with head or brain injury. The test biological sample can be an in vitro sample or an in vivo sample. In various embodiments, the subject is a human subject, and may be of any race, sex and age. Representative subjects include those who are suspected of having a head or brain injury, those who have been diagnosed with a head or brain injury, and those who are at risk of developing a head or brain injury.

In some embodiments, a miR-binding molecule is used in vivo for the diagnosis of head or brain injury. In some embodiments, the miR-binding molecule is a nucleic acid molecule, a protein or an antibody that hybridizes with a head or brain injury associated miR of the invention.

In one embodiment, the test sample is a sample containing a miR associated with head or brain injury. In one embodiment, the test sample is a sample containing an exosome, wherein the exosome contains a miR associated with head or brain injury.

In some embodiments, the test sample is prepared from a biological sample obtained from the subject. The biological sample can be a sample from any source which contains a miR associated with head or brain injury, such as a body fluid (e.g., blood, plasma, serum, saliva, urine, etc.), or a tissue, or an exosome, or a cell, or a combination thereof. A biological sample can be obtained by appropriate methods, such as, by way of examples, biopsy or fluid draw. The biological sample can be used as the test sample; alternatively, the biological sample can be processed to enhance access to polypeptides, nucleic acids, or copies of nucleic acids (e.g., copies of nucleic acids comprising a miR associated with head or brain injury), and the processed biological sample can then be used as the test sample. For example, in various embodiments, nucleic acid is prepared from a biological sample, for use in the methods. Alternatively or in addition, if desired, an amplification method can be used to amplify nucleic acids comprising all or a fragment of a nucleic acid in a biological sample, for use as the test sample in the assessment of the level of a miR associated with head or brain injury.

The test sample is assessed to determine the level of at least one miR associated with head or brain injury present in the sample of the subject. In general, detecting a miR may be carried out by determining the presence or absence of a nucleic acid containing a miR of interest in the test sample.

In certain embodiments, methods of measuring a miR associated with head or brain injury in a sample entails the use of, but is not limited to, fluorescent, radioactive, or marker based hybridization probes, hairpin probes, FRET (fluorescence resonance energy transfer) probes, molecular beacons, nano-flares, template reaction hybridization probes, PCR, quantitative PCR, RNase protection assays, hybridization or sequencing arrays, differential display, northern blotting, or other signal amplification assay.

In one embodiment, the method of measuring a miR associated with head or brain injury comprises mixing a sample and a probe for the miR to form a miR probe hybrid, optionally purifying the hybrid, and visualizing by mixing with an intercalating dye.

In one embodiment, the method of measuring a miR associated with head or brain injury comprises the use of probes that are radioactive and optionally separating the probes from probes that hybridize to the target miR wherein measuring radioactivity indicates the quantity of the probe that hybridizes to miR in the sample. In certain embodiments, the probe comprises a radioactive isotope of phosphorus $^{32}$P incorporated into the phosphodiester bond in the probe. The probe may be detected by visualizing the hybridized probe via autoradiography or other imaging techniques.

In one embodiment, the method of measuring a miR associated with head or brain injury comprises the use of probes that comprise antibody epitopes and optionally separate the probes from a probe that hybridizes to the target miR wherein measuring antibody binding, e.g., with an antibody conjugated to a fluorescent chromophore or other marker, e.g., enzyme, indicates the quantity of the probe that hybridizes to a miR associated with head or brain injury in the sample. In certain embodiments, the epitope is digoxigenin.

In one embodiment, the disclosure relates to methods comprising mixing the sample with a composition or surface comprising a probe that hybridizes to at least one miR associated with head or brain injury and detecting hybridization of the probe to the miR in the sample under conditions such that an amount of miR is quantified. In certain embodiments, a fluorescent probe sequence or a probe sequence is generated that can be rendered fluorescent later, e.g., a probe conjugated to a ligand that can bind a fluorescent receptor or a probe conjugated to a receptor that can bind a fluorescent ligand or a probe with two oligonucleotide sequences, one that can hybridize to the target and the second that can hybridize to a secondary detection oligonucleotide. The probe and target sequences are then mixed together, and the probe specifically hybridizes to its complementary sequence on the target. If the probe is already fluorescent, it will be possible to directly detect hybridization in the sample. In some instances, an additional step may be needed to visualize the hybridized probe. Hybrids formed between the probes and their targets can be detected using a fluorescent microscope or other visualization device. The intensity of the light signal correlates to the quantity of the target as can be evaluated in light of a standard or reference value using well-known analytical calibration techniques.

In certain embodiments, the probe comprises a FRET acceptor and FRET donor configured such that binding to the probe creates a light signal wherein measuring the intensity of the light signal indicates the quantity of a miR associated with head or brain injury in the sample. Upon exposure to certain wavelengths of electromagnetic radiation, e.g., visible or UV light, energy transfers can occur between two different chromophores, typically referred to as the donor or acceptor, when the chromophores are in short distance, on a molecular scale, to each other. This is referred to as fluorescence resonance energy transfer (FRET). Depending on the chromophores, this can cause a change in fluorescence wavelength emission or quenching. FRET probes are typically designed to have a pair of different chromophores covalently attached to an oligonucleotide sequence that is complementary to a nucleic acid target. In the absence of the target, the fluorescence of the chromophore reporter group is either quenched or generates a unique signal. When the target is added, the oligonucleotide-based probes hybridize to the target and produce a distinctive fluorescence signal or reduction thereof.

Binary probes typically utilized a fluorescence donor and a fluorescence acceptor that are tethered to the ends of two single-stranded oligonucleotides, which are complementary to adjacent regions of a target. When they are not exposed to the target, the two oligonucleotide probes are distributed randomly and separated by large distances, on a molecular scale, in solution. Hybridizing to the target brings the donor and acceptor into close proximity. Upon exciting, the close proximity of the donor to the acceptor results in quenching or other emission change that can be detected.

A molecular beacon refers to a hairpin probe that contains a single-stranded oligonucleotide loop with a chromophore and a quencher attached at its opposite strands of the stem. The central loop sequence is complementary to a target. The chromophore and quencher are arranged at each the stem strands to force the chromophore and quencher to be in close proximity. Hybridization to a target causes the chromophore and the quencher to spatially separate, on a molecular scale, creating a fluorescence change upon photoexcitation.

A scorpion probe is a modification of the molecular beacon wherein the loop sequence in the hairpin contains the target sequence. A single stranded probe sequence to the target or a portion of target, the reverse complement of the target, is added to the 5' end of the hairpin allowing for bind to the target and elongation over the entire length of the target in the presence of amplification reagents, e.g., polymerase and nucleotides. Upon completion of double strand synthesis at the target, the loop sequence hybridizes to the polymerase generated sequence causing separation of the chromophores producing a fluorescent signals.

Nano-flares may be used for detection or nucleic acids. For example, a nanoparticle, e.g., gold nanoparticle or quantum dot, acts as one of the chromophores for FRET. The nanoparticle is conjugated to an oligonucleotide probe containing the target sequence. Hybridized to the probe-nanoparticle conjugate is an oligonucleotide containing the shortened target sequence or portion thereof conjugated to a second chromophore for FRET. The second chromophore on the oligonucleotide is configured to be near the surface, on a molecular scale, of the nanoparticle upon hybridization. When the nanoparticle is exposed to the target, the oligonucleotide containing the shortened target sequence is displaced releasing the second chromophore for detection by photoexcitation.

Templated reaction probes typically utilize two probes that bind next each on a target sequence. The probes create a reactive group that results in a chemical reaction. This reaction can be controlled by effective concentration. The amount of a target sequences can be correlated to the signal resulting from the chemical reaction. Examples include templated photochemical reactions, ester-hydrolysis reactions, nucleophilic substitution reactions, fluorescence signal-generating reactions, photochemical cyclo-addition reactions, and peptide chemical reactions.

In certain embodiments, the disclosure relates to methods of detecting a miR associated with head or brain injury using PCR and quantitative PCR using primers, e.g., forward and reverse primers are designed to anneal to the stem portion of the hairpin. Polymerase chain reaction (PCR) may be used to quantify the amount of a nucleic acid in a sample. Quantitative PCR is different from standard PCR where the product of the reaction is detected at its end, i.e., by monitoring the reaction progresses in real time. Two typical methods for detection of products in quantitative PCR are non-specific fluorescent dyes that intercalate with any double-stranded nucleic acid, and sequence-specific probes that are labeled with a fluorescent reporter which permits detection only after hybridization of the probe with its complementary target. Detailed methods real-time PCR quantification of precursor and mature microRNA are reported in Schmittgen et al., Methods, 2008, 44(1): 31-38.

In certain embodiments, this disclosure relates to the use of quantitative PCR wherein a detection probe contain a chromophore covalently attached to one end, e.g., 5'-end of the probe, and a quencher at the other end, e.g., 3'-end. The quencher molecule quenches the fluorescence emitted by the chromophore when excited by a source of excitation (FRET). Hybridization probes target a region within a sequence to be amplified by a set of PCR primers. Taq polymerase extends the hybridization primer and synthesizes the nascent strand. The 5' to 3' exonuclease activity of the polymerase degrades the detection probe resulting in fluorescence due to separation of the donor and acceptor. The fluorescence signal correlates proportionally to the amount of nucleic acid.

In certain embodiments, quantitative PCR is performed by using a stem-loop primer containing a single stranded tail that hybridizes to one end, e.g., 3' or 5' end, of a miR. The stem-loop primer initially adds a polynucleotide sequence within the stem-loop to the end of microRNA resulting in a longer sequence creating more room for forward and reverse primer amplification and annealing of the detection probe, e.g., the added sequence in the stem-loop primer contains the template for a reverse primer in the loop sequence of the stem-loop primer and optionally a target sequence for all or a portion of the detection probe in the stem sequence of the stem-loop primer.

In some embodiments, hybridization methods, such as Northern analysis, or in situ hybridizations, can be used (see Current Protocols in Molecular Biology, 2012, Ausubel, F. et al., eds., John Wiley & Sons, including all supplements). For example, the presence of a miR associated with head or brain injury can be indicated by hybridization to a nucleic acid probe. A "nucleic acid probe," as used herein, can be a nucleic acid probe, such as a DNA probe or an RNA probe. For representative examples of use of nucleic acid probes, see, for example, U.S. Pat. Nos. 5,288,611 and 4,851,330.

Northern blotting may be used to visualize the amount of a target nucleic acid in a sample. A mixture of nucleic acids are separated by gel electrophoresis, transferred to a solid matrix (such as a nylon membrane), and mixed with target probes to provide qualitative or quantitative information of nucleic acid levels. In certain embodiments, a miR associated with head or brain injury is quantified by performing electrophoresis under conditions that separates a probe hybridized to a target miR, transferring the probe hybridized to the target miR to a medium, and visualizing the probe hybridized to the target miR on the medium.

To detect at least one miR of interest, a hybridization sample is formed by contacting the test sample with at least one nucleic acid probe. In one embodiment, a probe for detecting miR is a labeled nucleic acid probe capable of hybridizing to miR. The nucleic acid probe can be, for example, a full-length nucleic acid molecule, or a portion thereof, such as an oligonucleotide of at least 10, 15, or 25 nucleotides in length and sufficient to specifically hybridize under stringent conditions to appropriate miR. The hybridization sample is maintained under conditions which are sufficient to allow specific hybridization of the nucleic acid probe to a miR target of interest. Specific hybridization can be performed under high stringency conditions or moderate stringency conditions, as appropriate. In one embodiment, the hybridization conditions for specific hybridization are high stringency. Specific hybridization, if present, is then detected using standard methods. If specific hybridization occurs between the nucleic acid probe and a miR in the test sample, the sequence that is present in the nucleic acid probe is also present in the miR of the subject. More than one nucleic acid probe can also be used concurrently in this method. Specific hybridization of any one of the nucleic acid probes is indicative of the presence of the miR of interest, as described herein.

Alternatively, a peptide nucleic acid (PNA) probe can be used instead of a nucleic acid probe in the hybridization methods described herein. PNA is a DNA mimic having a peptide-like, inorganic backbone, such as N-(2-aminoethyl) glycine units, with an organic base (A, G, C, T or U) attached to the glycine nitrogen via a methylene carbonyl linker (see, for example, 1994, Nielsen et al., Bioconjugate Chemistry 5:1). The PNA probe can be designed to specifically hybridize to a nucleic acid sequence comprising at least one miR of interest. Hybridization of the PNA probe to a nucleic acid sequence is indicative of the presence of a miR of interest.

In certain embodiments, nuclease protection assays, e.g., ribonuclease protection assays (RPAs) and S1 nuclease assays may be used for the quantitation of a miR associated with head or brain injury. Probes, e.g., radiolabeled, are mixed with the sample to hybridize to the target. Remaining hybridized probes are removed by digestion with a mixture of nucleases followed by steps in which the nucleases are inactivated and probe-target hybrids are precipitated. These products are separated, e.g., on a denaturing polyacrylamide gel and are visualized by autoradiography. If non-isotopic probes are used, samples may be visualized by transferring the gel to a membrane and performing secondary detection with antibodies or other appropriate binding agent.

In certain embodiments, this disclosure relates to methods disclosed herein wherein the probe is radioactive further comprising the steps of measuring radioactivity and correlating radioactivity to the quantity of the probe that hybridizes to a target miR associated with head or brain injury in the sample.

In certain embodiments, this disclosure relates to methods disclosed herein wherein the probe is radioactive further comprising the step of mixing the composition with nucleases that specifically cleave single-stranded nucleic acids but do not cleave double-stranded nucleic acids In certain embodiments, methods disclosed herein include the steps of separating the probes from a probe that hybridizes to a target miR by mixing with a composition comprising nucleases that specifically cleave single-stranded nucleic acids but do not cleave double-stranded nucleic acids.

In certain embodiments, any of the methods disclosed herein may utilize a surface, wherein the surface comprises a probe conjugated to the surface. In certain embodiments, the surface is an array, bead, or nanoparticle.

In certain embodiment, for any of the methods disclosed herein, measuring is under conditions that a signal is produced and comparing the signal to a standard or reference value indicating the quantity of a target miR in the sample.

Direct sequence analysis can also be used to detect miRs of interest. A sample comprising nucleic acid can be used, and PCR or other appropriate methods can be used to amplify all or a fragment of the nucleic acid, and/or its flanking sequences, if desired.

In another embodiment, arrays of oligonucleotide probes that are complementary to target nucleic acid sequences from a subject can be used to detect, identify and quantify miRs associated with head or brain injury. For example, in one embodiment, an oligonucleotide array can be used. Oligonucleotide arrays typically comprise a plurality of different oligonucleotide probes that are coupled to a surface of a substrate in different known locations. These oligonucleotide arrays, also known as "Genechips," have been generally described in the art, for example, U.S. Pat. No. 5,143,854 and PCT patent publication Nos. WO 90/15070 and 92/10092. These arrays can generally be produced using mechanical synthesis methods or light directed synthesis methods which incorporate a combination of photolithographic methods and solid phase oligonucleotide synthesis methods. See Fodor et al., Science, 251:767-777 (1991), Pirrung et al., U.S. Pat. No. 5,143,854 (see also PCT Application No. WO 90/15070) and Fodor et al., PCT Publication No. WO 92/10092 and U.S. Pat. No. 5,424,186. Techniques for the synthesis of these arrays using mechanical synthesis methods are described in, e.g., U.S. Pat. No. 5,384,261.

After an oligonucleotide array is prepared, a sample containing miR is hybridized with the array and scanned for miRs. Hybridization and scanning are generally carried out by methods described herein and also in, e.g., Published PCT Application Nos. WO 92/10092 and WO 95/11995, and U.S. Pat. No. 5,424,186, the entire teachings of which are incorporated by reference herein.

In one embodiment, a target miR sequence can be amplified by well-known amplification techniques, e.g., RT, PCR. Typically, this involves the use of primer sequences that are complementary to the target miR. Amplified target, generally incorporating a label, is then hybridized with the array under appropriate conditions. Upon completion of hybridization and washing of the array, the array is scanned to determine the position on the array to which the target sequence hybridizes. The hybridization data obtained from the scan is typically in the form of fluorescence intensities as a function of location on the array.

Other methods of nucleic acid analysis can be used to detect miRs of interest. Representative methods include direct manual sequencing (1988, Church and Gilbert, Proc. Natl. Acad. Sci. USA 81:1991-1995; 1977, Sanger et al., Proc. Natl. Acad. Sci. 74:5463-5467; Beavis et al. U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE) (Sheffield et al., 1981, Proc. Natl. Acad. Sci. USA 86:232-236), mobility shift analysis (Orita et al., 1989, Proc. Natl. Acad. Sci. USA 86:2766-2770; Rosenbaum and Reissner, 1987, Biophys. Chem. 265:1275; 1991, Keen et al., Trends Genet. 7:5); RNase protection assays (Myers, et al., 1985, Science 230: 1242); Luminex xMAP™ technology; high-throughput sequencing (HTS) (Gundry and Vijg, 2011, Mutat Res, doi:10.1016/j.mrfmmm.2011.10.001); next-generation sequencing (NGS) (Voelkerding et al., 2009, Clinical Chemistry 55:641-658; Su et al., 2011, Expert Rev Mol Diagn. 11:333-343; Ji and Myllykangas, 2011, Biotechnol Genet Eng Rev 27:135-158); and/or ion semiconductor sequencing (Rusk, 2011, Nature Methods doi:10.1038/nmeth.f.330; Rothberg et al., 2011, Nature 475:348-352). These and other methods, alone or in combination, can be used to detect and quantity of at least one miR of interest, in a biological sample obtained from a subject. In one embodiment of the invention, the methods of assessing a biological sample to detect and quantify a miR of interest, as described herein, are used to diagnose, assess and characterize a head or brain injury in a subject in need thereof.

The probes and primers according to the invention can be labeled directly or indirectly with a radioactive or nonradioactive compound, by methods well known to those skilled in the art, in order to obtain a detectable and/or quantifiable signal; the labeling of the primers or of the probes according to the invention is carried out with radioactive elements or with nonradioactive molecules. Among the radioactive isotopes used, mention may be made of $^{32}$P, $^{33}$P, $^{35}$S or $^{3}$H. The nonradioactive entities are selected from ligands such as biotin, avidin, streptavidin or digoxigenin, haptenes, dyes, and luminescent agents such as radioluminescent, chemoluminescent, bioluminescent, fluorescent or phosphorescent agents.

Nucleic acids can be obtained from the biological sample using known techniques. Nucleic acid herein includes RNA, including mRNA, miR, etc. The nucleic acid can be double-stranded or single-stranded (i.e., a sense or an antisense single strand) and can be complementary to a nucleic acid encoding a polypeptide. The nucleic acid content may also be obtained from an extraction performed on a fresh or fixed biological sample.

There are many methods known in the art for the detection of specific nucleic acid sequences and new methods are continually reported. A great majority of the known specific nucleic acid detection methods utilize nucleic acid probes in specific hybridization reactions.

In the Northern blot method, the nucleic acid probe may be labeled with a tag. That tag can be a radioactive isotope, a fluorescent dye or the other well-known materials. Another type of process for the specific detection of nucleic acids of exogenous organisms in a body sample known in the art are the hybridization methods as exemplified by U.S. Pat. Nos. 6,159,693 and 6,270,974, and related patents. To briefly summarize one of those methods, a nucleic acid probe of at least 10 nucleotides, at least 15 nucleotides, or at least 25 nucleotides, having a sequence complementary to a desired region of the target nucleic acid of interest is hybridized in a sample, subjected to depolymerizing conditions, and the sample is treated with an ATP/luciferase system, which will luminesce if the nucleic sequence is present. In quantitative Northern blotting, levels of the polymorphic nucleic acid can be compared to wild-type levels of the nucleic acid.

A further process for the detection of hybridized nucleic acid takes advantage of the polymerase chain reaction (PCR). The PCR process is well known in the art (U.S. Pat. Nos. 4,683,195, 4,683,202, and 4,800,159). To briefly summarize PCR, nucleic acid primers, complementary to opposite strands of a nucleic acid amplification target nucleic acid sequence, are permitted to anneal to the denatured sample. A DNA polymerase (typically heat stable) extends the DNA duplex from the hybridized primer. The process is repeated to amplify the nucleic acid target. If the nucleic acid primers do not hybridize to the sample, then there is no corresponding amplified PCR product.

In PCR, the nucleic acid probe can be labeled with a tag as discussed before. In one embodiment, the detection of the duplex is done using at least one primer directed to the target nucleic acid. In yet another embodiment of PCR, the detection of the hybridized duplex comprises electrophoretic gel separation followed by dye-based visualization.

Nucleic acid amplification procedures by PCR are well known and are described in U.S. Pat. No. 4,683,202. Briefly, the primers anneal to the target nucleic acid at sites distinct from one another and in an opposite orientation. A primer annealed to the target sequence is extended by the enzymatic action of a heat stable polymerase. The extension product is then denatured from the target sequence by heating, and the process is repeated. Successive cycling of this procedure on both strands provides exponential amplification of the region flanked by the primers.

Amplification is then performed using a PCR-type technique, that is to say the PCR technique or any other related technique. Two primers, complementary to the target nucleic acid sequence are then added to the nucleic acid content along with a polymerase, and the polymerase amplifies the DNA region between the primers.

Stem-loop RT-PCR is a PCR method that is useful in the methods of the invention to amplify and quantify miRs of interest (See Caifu et al., 2005, Nucleic Acids Research 33:e179; Mestdagh et al., 2008, Nucleic Acids Research 36:e143; Varkonyi-Gasic et al., 2011, Methods Mol Biol. 744:145-57). Briefly, the method includes two steps: RT and real-time PCR. First, a stem-loop RT primer is hybridized to a miR molecule and then reverse transcribed with a reverse transcriptase. Then, the RT products are quantified using conventional real-time PCR.

The expression specifically hybridizing in stringent conditions refers to a hybridizing step in the process of the invention where the oligonucleotide sequences selected as probes or primers are of adequate length and sufficiently unambiguous so as to minimize the amount of non-specific binding that may occur during the amplification. The oligonucleotide probes or primers herein described may be prepared by any suitable methods such as chemical synthesis methods.

Hybridization is typically accomplished by annealing the oligonucleotide probe or primer to the template nucleic acid under conditions of stringency that prevent non-specific binding but permit binding of this template nucleic acid which has a significant level of homology with the probe or primer.

Among the conditions of stringency is the melting temperature (Tm) for the amplification step using the set of primers, which is in the range of about 50° C. to about 95° C. Typical hybridization and washing stringency conditions depend in part on the size (i.e., number of nucleotides in length) of the template nucleic acid or the oligonucleotide probe, the base composition and monovalent and divalent cation concentrations (Ausubel et al., 1994, eds Current Protocols in Molecular Biology).

In one embodiment, the process for determining the level of at least one miR in a sample involves the use of real-time amplification performed using a labeled probe capable of specifically hybridizing in stringent conditions with a segment of a nucleic acid sequence, or polymorphic nucleic acid sequence. The labeled probe is capable of emitting a detectable signal every time each amplification cycle occurs.

The real-time amplification, such as real-time PCR, is well known in the art, and the various known techniques can be employed for the implementation of the present process. These techniques can be performed using various categories of probes, such as hydrolysis probes, hybridization adjacent probes, or molecular beacons. The techniques employing hydrolysis probes or molecular beacons are based on the use of a fluorescence quencher/reporter system, and the hybridization adjacent probes are based on the use of fluorescence acceptor/donor molecules.

Hydrolysis probes with a fluorescence quencher/reporter system are available in the market, and are for example commercialized by the Applied Biosystems group (USA). Many fluorescent dyes may be employed, such as FAM dyes (6-carboxy-fluorescein), or any other dye phosphoramidite reagents.

Among the stringent conditions applied for any one of the hydrolysis-probes of the present invention is the Tm, which is in the range of about 50° C. to 95° C. In one embodiment, the Tm for any one of the hydrolysis-probes of the present invention is in the range of about 55° C. to about 80° C. In one embodiment, the Tm applied for any one of the hydrolysis-probes of the present invention is about 75° C.

In one aspect, the invention includes a primer that is complementary to a nucleic acid sequence of a miR of interest, and more particularly the primer includes 12 or more contiguous nucleotides substantially complementary to the sequence of the miR of interest. In one embodiment, a primer featured in the invention includes a nucleotide sequence sufficiently complementary to hybridize to a nucleic acid sequence of about 12 to 25 nucleotides. In one embodiment, the primer differs by no more than 1, 2, or 3 nucleotides from the target nucleotide sequence. In another aspect, the length of the primer can vary in length, for example from about 15 to 28 nucleotides in length (e.g., 15, 16, 17, 18, 19, 20, 21, 22, 23, 24, 25, 26, 27 or 28 nucleotides in length).

Compositions

In one embodiment, the present invention provides therapeutic compositions for the treatment of a head or brain injury. In various embodiments, the therapeutic compositions include but are not limited to, activators and inhibitors of at least one miR of the invention. In one embodiment, the therapeutic compositions comprise at least one miR of the invention.

In one embodiment, the invention relates to compositions for use in increasing the level of a miR that has been identified as decreased in head or brain injury. In one embodiment, such a composition is an activator of the expression or activity of a miR that has been identified as decreased in head or brain injury. Activators are compounds that increase, open, activate, facilitate, enhance activation, sensitize, agonize, or up regulate activity or expression of a marker.

In one embodiment, administration of a miR to a subject serves to increase the activity of the miR in the subject. Therefore, in one embodiment, the invention relates to a therapeutic composition comprising one or more of miR-7844-5p, miR-144-5p, miR-221-5p, and miR-22-3p. In one embodiment, a composition for use in treating head or brain injury comprises miR-7844-5p.

In one embodiment, the invention provides short nucleic acid molecules that function as miRs. The term "short" refers to a length of a single polynucleotide that is 150 nucleotides or fewer. In some instances, the nucleic acid molecules are synthetic. The term "synthetic" means the nucleic acid molecule is isolated and not identical in sequence (the entire sequence) and/or chemical structure to a naturally-occurring nucleic acid molecule, such as an endogenous precursor miR molecule. While in some embodiments, nucleic acids of the invention do not have an entire sequence that is identical to a sequence of a naturally-occurring nucleic acid, such molecules may encompass all or part of a naturally-occurring sequence. It is contemplated, however, that a synthetic nucleic acid administered to a cell may subsequently be modified or altered in the cell such that its structure or sequence is the same as non-synthetic or naturally occurring nucleic acid, such as a mature miR sequence. For example, a synthetic nucleic acid may have a sequence that differs from the sequence of a precursor miR, but that sequence may be altered once in a cell to be the same as an endogenous, processed miR. The term "isolated" means that the nucleic acid molecules of the invention are initially separated from different (in terms of sequence or structure) and unwanted nucleic acid molecules such that a population of isolated nucleic acids is at least about 90% homogenous, and may be at least about 95, 96, 97, 98, 99, or 100% homogenous with respect to other polynucleotide molecules. In many embodiments of the invention, a nucleic acid is isolated by virtue of it having been synthesized in vitro separate from endogenous nucleic acids in a cell. It will be understood, however, that isolated nucleic acids may be subsequently mixed or pooled together.

While many of the embodiments of the invention involve synthetic miRs or synthetic nucleic acids, in some embodiments of the invention, the nucleic acid molecule(s) need not be "synthetic." In certain embodiments, a non-synthetic miR employed in methods and compositions of the invention may have the entire sequence and structure of a naturally occurring miR precursor or the mature miR. For example, non-synthetic miRs used in methods and compositions of the invention may not have one or more modified nucleotides or nucleotide analogs. In these embodiments, the non-synthetic miR may or may not be recombinantly produced. In particular embodiments, the nucleic acid in methods and/or compositions of the invention is specifically a synthetic miR and not a non-synthetic miR (that is, not an miR that qualifies as "synthetic"); though in other embodiments, the invention specifically involves a non-synthetic miR and not a synthetic miR. Any embodiments discussed with respect to the use of synthetic miRs can be applied with respect to non-synthetic miRs, and vice versa.

In certain embodiments, synthetic miRNA have a) an "miRNA region" whose sequence from 5' to 3' is identical to a mature miRNA sequence, and b) a "complementary region" whose sequence from 5' to 3' is between 60% and 100% complementary to the miRNA sequence. In certain embodiments, these synthetic miRNA are also isolated, as defined above. The term "miRNA region" refers to a region on the synthetic miRNA that is at least 90% identical to the entire sequence of a mature, naturally occurring miRNA sequence. In certain embodiments, the miRNA region is or is at least 90, 91, 92, 93, 94, 95, 96, 97, 98, 99, 99.1, 99.2, 99.3, 99.4, 99.5, 99.6, 99.7, 99.8, 99.9 or 100% identical to the sequence of a naturally-occurring miRNA.

In some embodiments, of the invention, a synthetic miRNA contains one or more design elements. These design elements include, but are not limited to: i) a replacement group for the phosphate or hydroxyl of the nucleotide at the 5' terminus of the complementary region; ii) one or more sugar modifications in the first or last 1 to 6 residues of the complementary region; or, iii) noncomplementarity between one or more nucleotides in the last 1 to 5 residues at the 3' end of the complementary region and the corresponding nucleotides of the miRNA region.

In certain embodiments, a synthetic miRNA has a nucleotide at its 5' end of the complementary region in which the phosphate and/or hydroxyl group has been replaced with another chemical group (referred to as the "replacement design"). In some cases, the phosphate group is replaced, while in others, the hydroxyl group has been replaced. In particular embodiments, the replacement group is biotin, an amine group, a lower alkylamine group, an acetyl group, 2'O-Me (2' oxygen-methyl), DMTO (4,4'-dimethoxytrityl with oxygen), fluoroscein, a thiol, or acridine, though other replacement groups are well known to those of skill in the art and can be used as well.

Additional embodiments concern a synthetic miR having one or more sugar modifications in the first or last 1 to 6 residues of the complementary region (referred to as the "sugar replacement design"). In certain cases, there is one or more sugar modifications in the first 1, 2, 3, 4, 5, 6 or more residues of the complementary region, or any range derivable therein. In additional cases, there is one or more sugar modifications in the last 1, 2, 3, 4, 5, 6 or more residues of the complementary region, or any range derivable therein, have a sugar modification. It will be understood that the terms "first" and "last" are with respect to the order of residues from the 5' end to the 3' end of the region. In particular embodiments, the sugar modification is a 2'O-Me modification. In further embodiments, there is one or more sugar modifications in the first or last 2 to 4 residues of the complementary region or the first or last 4 to 6 residues of the complementary region.

In one embodiment, the invention relates to compositions for use in decreasing the level of a miR that has been identified as increased in head or brain injury. In one embodiment, such a composition is an inhibitor of the expression or activity of a miR that has been identified as increased in head or brain injury. Inhibitors are compounds that, e.g., bind to, partially or totally block activity, decrease, prevent, delay activation, inactivate, desensitize, or down regulate the activity or expression of a marker.

In one embodiment, the invention relates to compositions for use in increasing or decreasing the level of at least one gene that this regulated by a miR associated with head or brain injury. In one embodiment, the invention relates to a composition that increases or decreases the level of at least one gene that this regulated by miR-7844-5p. Genes downregulated by miR-7844-5p include, but are not limited to LIMS1, CLDND1, CLDN12, OCLN, TJP1, F11R, ATG12, MAP1LC3E, ATG13, ATG14, CDK2, MAPK8, CDK13, SPP1, CDK8, MAPK3, CKD15, CDK6, CDK12, CDK17, ITGA1, MAPK14, MAPK1, MAPK13, GSK3B, ITGB8, ITGA7, ITGA8, ITGB6, ITGA2, ITGB3 and STUB1. Therefore, in one embodiment, the therapeutic composition of the invention decreases the level of one or more of LIMS1, CLDND1, CLDN12, OCLN, TJP1, F11R, ATG12, MAP1LC3E, ATG13, ATG14, CDK2, MAPK8, CDK13, SPP1, CDK8, MAPK3, CKD15, CDK6, CDK12, CDK17, ITGA1, MAPK14, MAPK1, MAPK13, GSK3B, ITGB8, ITGA7, ITGA8, ITGB6, ITGA2, ITGB3 and STUB1. In one embodiment, the therapeutic composition of the invention decreases the level of one or more of LIMS1, CLDND1, CDK2, MAPK8, CDK13, SPP1, CDK8, MAPK3, CKD15, CDK6, CDK12, CDK17, ITGA1, MAPK14, and MAPK1.

Modulators of miR

In one embodiment, the invention relates to compositions comprising modulators (i.e. activators or inhibitors) for use in increasing or decreasing a level of a miR, pre-miR or at least one gene regulated by a miR. As used herein, in general, the terms "activator" and "inhibitor" include but are not limited to a protein, a polypeptide, a peptide, a nucleic acid including, an oligonucleotide or modified oligonucleotide, an antisense oligonucleotide or modified antisense oligonucleotide, cDNA, genomic DNA, an artificial or natural chromosome (e.g. a yeast artificial chromosome) or a part thereof, RNA, including mRNA, tRNA, rRNA or a ribozyme, a peptide nucleic acid (PNA), a nucleotide, a ribonucleotide, a synthetic analog of a nucleotide, a synthetic analog of a ribonucleotide, a modified nucleotide, a modified ribonucleotide, an amino acid, an amino acid analog, a modified amino acid, a modified amino acid analog, a steroid, a proteoglycan, a lipid, a fatty acid and a carbohydrate. A modulator may be in solution or in suspension (e.g., in crystalline, colloidal or other particulate form). The modulator may be in the form of a monomer, dimer, oligomer, etc, or otherwise in a complex.

In certain embodiments, the composition comprises a modulator that increases the expression or activity of a miR. In one embodiment, the composition comprises a miR, a pre-miR or a miR mimic. In one embodiment, a miR mimics is a small, chemically modified double-stranded RNA that mimics endogenous miRs and increases miR activity. In one embodiment, the composition comprises a nucleic acid molecule that encodes a miR or a miR mimic. In certain embodiments, the miR is at least one of miR-7844-5p, miR-144-5p, miR-221-5p, and miR-22-3p.

In certain embodiments, the composition comprises a modulator that decreases the expression or activity of a miR. Therefore, in one embodiment the composition comprises a miR inhibitor. In one embodiment, a miR inhibitor is a small, chemically modified single-stranded RNA molecules designed to specifically bind to and inhibit endogenous miR molecules (e.g. an anti-miR). In one embodiment, the composition comprises a nucleic acid molecule that encodes a miR inhibitor. In one embodiment, the miR is at least one of miR-92b-5p, miR-423-5p, and miR-24-3p.

miRs are small non-coding RNA molecules that are capable of causing post-transcriptional silencing of specific genes in cells by the inhibition of translation or through degradation of the targeted mRNA. A miR can be completely complementary or can have a region of noncomplementarity with a target nucleic acid, consequently resulting in a "bulge" at the region of non-complementarity. A miR can inhibit gene expression by repressing translation, such as when the miR is not completely complementary to the target nucleic acid, or by causing target RNA degradation, which is believed to occur only when the miR binds its target with perfect complementarity. The disclosure also can include double-stranded precursors of miR. A miR can be 18-100 nucleotides in length, and more preferably from 18-80 nucleotides in length. Mature miRs can have a length of 19-30 nucleotides, preferably 21-25 nucleotides, particularly 21, 22, 23, 24, or 25 nucleotides. miR precursors typically have a length of about 70-100 nucleotides and have a hairpin conformation. miRs are generated in vivo from pre-miRs by the enzymes Dicer and Drosha, which specifically process long pre-miR into functional miR. The hairpin or mature microRNAs, or pri-microRNA agents featured in the disclosure can be synthesized in vivo by a cell-based system or in vitro by chemical synthesis. In one embodiment, a modulator of a miR is a modulator of a miR precursor, e.g. a modulator of a pre-miR.

In various embodiments, agent comprises an oligonucleotide that contains the nucleotide sequence of at least one of miR-7844-5p, miR-144-5p, miR-221-5p, miR-22-3p, miR- 92b-5p, miR-423-5p, and miR-24-3p. In certain embodiments, the oligonucleotide comprises the nucleotide sequence of a miR in a pre-miR, mature or hairpin form. In other embodiments, a combination of oligonucleotides comprising a sequence of one or more miRs, any pre-miR, any fragment, or any combination thereof is envisioned.

miR compositions, including, but not limited to, compositions comprising miRs, pre-miRs, miR mimics, and anti-miRs, can be synthesized to include a modification that imparts a desired characteristic. For example, the modification can improve stability, hybridization thermodynamics with a target nucleic acid, targeting to a particular tissue or cell-type, or cell permeability, e.g., by an endocytosis-dependent or -independent mechanism.

Modifications can also increase sequence specificity, and consequently decrease off-site targeting. Methods of synthesis and chemical modifications are described in greater detail below. If desired, miR compositions, including, but not limited to, compositions comprising miRs, pre-miRs, miR mimics, and anti-miRs, may be modified to stabilize the oligonucleiotide molecules against degradation, to enhance half-life, or to otherwise improve efficacy. Desirable modifications are described, for example, in U.S. Patent Publication Nos. 20070213292, 20060287260, 20060035254. 20060008822. and 2005028824, each of which is hereby incorporated by reference in its entirety. For increased nuclease resistance and/or binding affinity to the target, the single-stranded oligonucleotide agents featured in the disclosure can include 2'-O-methyl, 2'-fluorine, 2'-O-methoxyethyl, 2'-O-aminopropyl, 2'-amino, and/or phosphorothioate linkages. Inclusion of locked nucleic acids (LNA), ethylene nucleic acids (ENA), e.g., 2'-4'-ethylene-bridged nucleic acids, and certain nucleotide modifications can also increase binding affinity to the target. The inclusion of pyranose sugars in the oligonucleotide backbone can also decrease endonucleolytic cleavage. A oligonucleotide can be further modified by including a 3' cationic group, or by inverting the nucleoside at the 3'-terminus with a 3-3' linkage. In another alternative, the 3'-terminus can be blocked with an aminoalkyl group. Other 3' conjugates can inhibit 3'-5' exonucleolytic cleavage. While not being bound by theory, a 3' may inhibit exonucleolytic cleavage by sterically blocking the exonuclease from binding to the 3' end of the oligonucleotide. Even small alkyl chains, aryl groups, or heterocyclic conjugates or modified sugars (D-ribose, deoxyribose, glucose etc.) can block 3'-5'-exonucleases.

In one embodiment, the miR, pre-miR, miR mimic, or anti-miR includes a 2'-modified oligonucleotide containing oligodeoxynucleotide gaps with some or all internucleotide linkages modified to phosphorothioates for nuclease resistance. The presence of methylphosphonate modifications increases the affinity of the oligonucleotide for its target RNA and thus reduces the $IC_5Q$. This modification also increases the nuclease resistance of the modified oligonucleotide. It is understood that the methods and reagents of the present disclosure may be used in conjunction with any technologies that may be developed to enhance the stability or efficacy of an inhibitory nucleic acid molecule.

In one embodiment, the miR molecules including, but not limited to, molecules comprising miRs, pre-miRs, miR mimics, and anti-miRs, include nucleotide oligomers containing modified backbones or non-natural internucleoside linkages. Oligomers having modified backbones include those that retain a phosphorus atom in the backbone and those that do not have a phosphorus atom in the backbone. For the purposes of this disclosure, modified oligonucleotides that do not have a phosphorus atom in their internucleoside backbone are also considered to be nucleotide oligomers. Nucleotide oligomers that have modified oligonucleotide backbones include, for example, phosphorothioates, chiral phosphorothioates, phosphorodithioates, phosphotriesters, aminoalkyl-phosphotriesters, methyl and other alkyl phosphonates including 3'-alkylene phosphonates and chiral phosphonates, phosphinates, phosphoramidates, thionophosphoramidates, thionoalkylphosphonates, thionoalkylphosphotriesters, and boranophosphates. Various salts, mixed salts and free acid forms are also included. Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Nucleotide oligomers having modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyl eneimino and methylenehydrazino backbones; sulfonate and sulfonamide backbones; amide backbones; and others having mixed N, O, S and $CH_2$ component parts. Representative United States patents that teach the preparation of the above oligonucleotides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference. Nucleotide oligomers may also contain one or more substituted sugar moieties. Such modifications include 2'-O-methyl and 2'-methoxyethoxy modifications. Another desirable modification is 2'-dimethylaminooxyethoxy, 2'-aminopropoxy and 2'-fluoro. Similar modifications may also be made at other positions on an oligonucleotide or other nucleotide oligomer, particularly the 3' position of the sugar on the 3' terminal nucleotide. Nucleotide oligomers may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

In other nucleotide oligomers, both the sugar and the internucleoside linkage, i.e., the backbone, are replaced with groups. Methods for making and using these nucleotide oligomers are described, for example, in "Peptide Nucleic Acids (PNA): Protocols and Applications" Ed. P. E. Nielsen, Horizon Press, Norfolk, United Kingdom, 1999. Representative United States patents that teach the preparation of PNAs include, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

In other embodiments, a single stranded modified nucleic acid molecule (e.g., a nucleic acid molecule comprising a phosphorothioate backbone and 2'-OMe sugar modifications is conjugated to cholesterol.

A miR or miR mimic described herein, which may be in the pre-miR, mature or hairpin form, may be provided as a naked oligonucleotide that is capable of entering a cell. In some cases, it may be desirable to utilize a formulation that aids in the delivery of a miR or other nucleotide oligomer to cells (see, e.g., U.S. Pat. Nos. 5,656,611, 5,753,613, 5,785,992, 6,120,798, 6,221,959, 6,346,613, and 6,353,055, each of which is hereby incorporated by reference).

In some examples, the miR, pre-miR, miR mimic or anti-miR composition is at least partially crystalline, uniformly crystalline, and/or anhydrous (e.g., less than 80, 50, 30, 20, or 10% water). In another example, the miR, pre-miR, miR mimic or anti-miR composition is in an aqueous phase, e.g., in a solution that includes water. The aqueous phase or the crystalline compositions can be incorporated into a delivery vehicle, e.g., a liposome (particularly for the aqueous phase), or a particle (e.g., a microparticle as can be appropriate for a crystalline composition). Generally, the miR composition is formulated in a manner that is compatible with the intended method of administration. The miR, pre-miR, miR mimic or anti-miR composition can be formulated in combination with another agent, e.g., another therapeutic agent or an agent that stabilizes an oligonucleotide agent, e.g., a protein that complexes with the oligonucleotide agent. Still other agents include chelators, e.g., EDTA (e.g., to remove divalent cations such as Mg), salts, and RNAse inhibitors (e.g., a broad specificity RNAse inhibitor). In one embodiment, the miR, pre-miR, miR mimic or anti-miR composition includes another miR, pre-miR, miR mimic or anti-miR, e.g., a second miR, pre-miR, miR mimic or anti-miR composition (e.g., a miR that is distinct from the first). Still other preparations can include at least three, at least five, at least ten, at least twenty, at least fifty, or a at least hundred or more different oligonucleotide species.

miR mimics can mimic the activity of a miR through inhibiting one or more genes targeted by suppressor miR-NAs and consequently normalize cellular processes. Therefore, in one embodiment, the composition comprises an oligonucleotide composition that mimics the activity of a miR described herein. In certain embodiments, the composition comprises oligonucleotides having nucleobase identity to the nucleobase sequence of a miR, and are thus designed to mimic the activity of the miR. In certain embodiments, the oligonucleotide composition that mimics miR activity comprises a double-stranded RNA molecule which mimics the mature miR hairpins or processed miR duplexes. In one embodiment, a miR mimic is an LNA-modified oligonucleotide.

In one embodiment, the oligonucleotide shares identity with endogenous miR or miR precursor nucleobase sequences. An oligonucleotide selected for inclusion in a composition of the present invention may be one of a number of lengths. Such an oligonucleotide can be from 7 to 100 linked nucleosides in length. For example, an oligonucleotide sharing nucleobase identity with a miR may be from 7 to 30 linked nucleosides in length. An oligonucleotide sharing identity with a miR precursor may be up to 100 linked nucleosides in length. In certain embodiments, an oligonucleotide comprises 7 to 30 linked nucleosides. In certain embodiments, an oligonucleotide comprises 7, 8, 9, 10, 11, 12, 13, 14, 15, 16, 17, 18, 19, 20, 21, 22, 23, 24, 25, 26, 28, 29, or 30 linked nucleotides. In certain embodiments, an oligonucleotide comprises 19 to 23 linked nucleosides. In certain embodiments, an oligonucleotide is from 40 up to 50, 60, 70, 80, 90, or 100 linked nucleosides in length.

In certain embodiments, an oligonucleotide has a sequence that has a certain identity to a miR or a precursor thereof. Nucleobase sequences of mature miRs and their corresponding stem-loop sequences described herein are the sequences found in miRBase, an online searchable database of miR sequences and annotation. Entries in the miRBase Sequence database represent a predicted hairpin portion of a miR transcript (the stem-loop), with information on the location and sequence of the mature miR sequence. The miR stem-loop sequences in the database are not strictly precursor miRs, and may in some instances include the pre-miR and some flanking sequence from the presumed primary transcript. The miR nucleobase sequences described herein encompass any version of the miR, including the sequences described in Release 10.0 of the miRBase sequence database and sequences described in any earlier Release of the miRBase sequence database. A sequence database release may result in the re-naming of certain miRs. A sequence database release may result in a variation of a mature miR sequence. The compositions of the present invention encompass oligomeric compound comprising oligonucleotides having a certain identity to any nucleobase sequence version of a miRs described herein.

In certain embodiments, an oligonucleotide has a nucleobase sequence at least 60%, 65%, 70%, 75%, 80%, 85%, 90%, 95%, 97%, 98% or 99% identical to the miR over a region of 7, 8, 9, 10, 11, 12, 13, 14, 15, 16, 17, 18, 19, 20, 21, 22, 23, 24, 25, 26, 27, 28, 29, or 30 nucleobases. Accordingly, in certain embodiments the nucleobase sequence of an oligonucleotide may have one or more non-identical nucleobases with respect to the miR.

In certain embodiments, the composition comprises a nucleic acid molecule encoding a miR, precursor, mimic, or fragment thereof. For example, the composition may comprise a viral vector, plasmid, cosmid, or other expression vector suitable for expressing the miR, precursor, mimic, or fragment thereof in a desired mammalian cell or tissue.

Small Molecule Inhibitors of miRs

Small molecules, including inorganic and organic chemicals, peptides and peptoids, have been reported as small molecule drugs targeting specific miRs (SMIRs). Therefore, in one embodiment, the invention relates to compositions comprising a small molecule inhibitor of a miR of the invention. In one embodiment, a small molecule of the invention will have specific binding affinity to a mature miR or a pre-miR. In one embodiment, the composition comprises a SMIR targeting at least one of miR-92b-5p, miR-423-5p, and miR-24-3p.

Anti-miR Oligonucleotides

Anti-miR oligonucleotides (AMOs) are generally single-stranded, chemically modified DNA-like molecules that are designed to be complementary to and inhibit a selected miR. In one embodiment, the composition comprises an AMO targeting at least one of miR-92b-5p, miR-423-5p, and miR-24-3p. miRs are incorporated into ribonucleoprotein particles (miRNPs) which predominantly act as translational repressors. AMOs are single stranded anti-microRNA molecules which are capable of inhibiting miRNP activity.

In one embodiment, the AMO is a modified oligonucleotides. In one embodiment, the phosphate backbone of the AMO is modified. A modification of an AMO may include, but is not limited to, a LNA modification, a morpholino modification and a chemical modification. LNA is a bicyclic RNA analogue in which the ribose is locked in a C3'-endo conformation by introduction of a 2'-O,4'-C methylene bridge. Morpholinos are uncharged, inherently resistant to degradation by nucleases. A representative United States patent application that teaches the preparation of such AMOs is published U.S. Application No. 20050182005A1 which is hereby incorporated by reference in its entirety.

In one embodiment, the invention includes a vector for expression of an anti-miR of the invention. In one embodiment, the vector is an expression vector designed to mediate the delivery of small RNAs in mammalian cells. In one embodiment, the expression vector is designed to stably express an anti-miR of the invention. The anti-miR oligonucleotide can be cloned into a number of types of vectors, including but not limited to lentiviral expression vectors.

In order to assess the expression of the anti-miR oligonucleotide, the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neomycin resistance and the like.

Alternatively, anti-miR oligonucleotides of the invention may be made synthetically and then provided to the cell. Compositions and methods for the synthesis and administration of anti-miR oligonucleotides are as described elsewhere herein.

miR Sponges

In one embodiment, an inhibitor of a miR of the invention may be in the form of a miR sponge. miR sponges are RNA transcripts produced from transgenes expressed in cells that contain multiple binding sites for a target miR. In one embodiment, a miR sponge may be expressed in a cell using an expression vector and administered using gene therapy methods. In one embodiment, a miR sponge of the invention targets one or more of miR-92b-5p, miR-423-5p, and miR-24-3p.

Methods of Treatment

Methods for increasing or decreasing the level, activity or expression of the markers of the present invention are well known and within the skill of a person in the art. A non-limitative list of known methods includes: gene therapy methods, miR replacement therapy methods, methods of treatment using antisense oligonucleotides, and methods of administering drugs and medications.

In one embodiment, the method of treatment includes administering to a subject in need thereof an effective amount of an activator or inhibitor of the invention. In one embodiment, the method of treatment includes administering to a subject in need thereof an effective amount of a composition comprising at least one miR. In one embodiment, the composition comprises miR-7844-5p.

Genetic Modification

The invention encompasses expression vectors and methods for the introduction of exogenous DNA into cells with concomitant expression of the exogenous DNA in the cells such as those described, for example, in Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York).

The desired polynucleotide can be cloned into a number of types of vectors. However, the present invention should not be construed to be limited to any particular vector. Instead, the present invention should be construed to encompass a wide plethora of vectors which are readily available and/or well-known in the art. For example, a desired polynucleotide of the invention can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2012), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

For expression of the desired polynucleotide, at least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 genes, a discrete element overlying the start site itself helps to fix the place of initiation.

Additional promoter elements, i.e., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either co-operatively or independently to activate transcription.

Naturally, it will be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al. (2012). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

The expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000 FEBS Lett. 479:79-82). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of siRNA polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In the context of an expression vector, the vector can be readily introduced into a host cell, e.g., mammalian, bacterial, yeast or insect cell by any method in the art. For example, the expression vector can be transferred into a host cell by physical, chemical or biological means. It is readily understood that the introduction of the expression vector comprising the polynucleotide of the invention yields a silenced cell with respect to a regulator.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2012, Molecular Cloning: A Laboratory Manual, Cold Spring Harbor Laboratory, New York), and in Ausubel et al. (1997, Current Protocols in Molecular Biology, John Wiley & Sons, New York).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Any DNA vector or delivery vehicle can be utilized to transfer the desired polynucleotide to a cell in vitro or in vivo. In the case where a non-viral delivery system is utilized, a preferred delivery vehicle is a liposome. The above-mentioned delivery systems and protocols therefore can be found in Gene Targeting Protocols, 2ed., pp 1-35 (2002) and Gene Transfer and Expression Protocols, Vol. 7, Murray ed., pp 81-89 (1991).

"Liposome" is a generic term encompassing a variety of single and multilamellar lipid vehicles formed by the generation of enclosed lipid bilayers or aggregates. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers. However, the present invention also encompasses compositions that have different structures in solution than the normal vesicular structure. For example, the lipids may assume a micellar structure or merely exist as nonuniform aggregates of lipid molecules. Also contemplated are lipofectamine-nucleic acid complexes.

Methods of Modulating miR Activity

MicroRNA activity can be modulated using any method disclosed herein or known to the skilled artisan. Examples of methods to enhance miR activity include but are not limited to, increasing expression of an endogenous miR-7844-5p, increasing the level of a miR by providing exogenous miR, and enhancing the function, activity, or stability of a miR. A miR activator may therefore be a compound that increases expression of an endogenous miR, increases the level of exogenous miR, or enhances one or more of the function, activity, or stability of a miR. A miR activator may be any type of compound, including but not limited to, a polypeptide, a protein (e.g., a transcription factor), a nucleic acid, an aptamer, a miR mimic, a pri-miR, a pre-miR and a small molecule, or combinations thereof.

Examples of methods to inhibit miR activity include but are not limited to, inhibiting expression of an endogenous miR, decreasing the level of a miR using an exogenous anti-miR, and inhibiting the function, activity, or stability of a miR. A miR inhibitor may therefore be a compound that decreases expression of a miR, decreases a miR half-life, stability and/or level, or inhibits miR function, activity or stability. A miR inhibitor may be any type of compound, including but not limited to, a polypeptide, a nucleic acid, an aptamer, an anti-miR, antagomiR, a miR sponge, a silencing RNA (siRNA), a short hairpin RNA (shRNA), a morpholino, a piwi-interacting RNA (piRNA), a repeat associated small interfering RNA (rasiRNAs), and a small molecule, or combinations thereof.

MicroRNA regulation may be accomplished either directly or indirectly. For example, a miR may be directly inhibited by compounds or compositions that directly interact with the miR, such as antibodies. Alternatively, a miR may be inhibited indirectly by compounds or compositions that inhibit miR downstream effectors, or upstream regulators which up-regulate miR expression.

Decreasing expression of an endogenous miR includes providing a specific inhibitor of miR expression. Decreasing expression of a miR includes decreasing the half-life or stability of a miR. Methods of decreasing expression of a miR include, but are not limited to, methods that use an siRNA, a microRNA, an antisense nucleic acid, a ribozyme, an expression vector encoding a transdominant negative mutant, a peptide, a small molecule, other specific inhibitors of a miR, and combinations thereof.

It will be appreciated that the compounds of the invention may be administered to a subject either alone, or in conjunction with another therapeutic agent. Agents that are found to be capable of modulating the level of at least one miR may be used, for example, to reduce the symptoms of head or brain injury alone or in combination with other appropriate agents or treatments. Well known treatments for head or brain injury include, but are not limited to, reduction of intracranial pressure, surgery, cognitive therapy, occupational therapy, speech therapy, physiotherapy, administration of pharmaceuticals, pain killers, rest from physical activity, restriction from certain activities and neuropsychological evaluation. Pain killers used for the treatment of head or brain injury include acetaminophen.

Gene Therapy Administration

One skilled in the art recognizes that different methods of delivery may be utilized to administer a nucleic acid molecule into a cell. Examples include: (1) methods utilizing physical means, such as electroporation (electricity), a gene gun (physical force) or applying large volumes of a liquid (pressure); and (2) methods wherein said molecule is complexed to another entity, such as a liposome, aggregated protein or transporter molecule.

Furthermore, the actual dose and schedule can vary depending on whether the compositions are administered in combination with other pharmaceutical compositions, or depending on inter-individual differences in pharmacokinetics, drug disposition, and metabolism. Similarly, amounts can vary in in vitro applications depending on the particular cell line utilized (e.g., based on the number of vector receptors present on the cell surface, or the ability of the particular vector employed for gene transfer to replicate in that cell line). Furthermore, the amount of nucleic acid molecule to be added per cell will likely vary with the length and stability of the therapeutic gene or miR, as well as the nature of the sequence, and the nature of the molecule (e.g. whether the therapeutic gene or miR is incorporated into an expression vector), and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

Cells containing the therapeutic agent may also contain a suicide gene i.e., a gene which encodes a product that can be used to destroy the cell. In many gene therapy situations, it is desirable to be able to express a gene for therapeutic purposes in a host, cell but also to have the capacity to destroy the host cell at will. The therapeutic agent can be linked to a suicide gene, whose expression is not activated in the absence of an activator compound. When death of the cell in which both the agent and the suicide gene have been introduced is desired, the activator compound is administered to the cell thereby activating expression of the suicide gene and killing the cell. Examples of suicide gene/prodrug combinations which may be used are herpes simplex virus-thymidine kinase (HSV-tk) and ganciclovir, acyclovir; oxidoreductase and cycloheximide; cytosine deaminase and 5-fluorocytosine; thymidine kinase thymidilate kinase (Tdk::Tmk) and AZT; and deoxycytidine kinase and cytosine arabinoside.

Dosage and Formulation

The present invention envisions treating a head or brain injury in a subject by the administration of therapeutic agent, e.g. an activator or inhibitor of a miR associated with head or brain injury.

Administration of the therapeutic agent in accordance with the present invention may be continuous or intermittent, depending, for example, upon the recipient's physiological condition, whether the purpose of the administration is therapeutic or prophylactic, and other factors known to skilled practitioners. The administration of the agents or modified cell of the invention may be essentially continuous over a preselected period of time or may be in a series of spaced doses. Both local and systemic administration is contemplated. The amount administered will vary depending on various factors including, but not limited to, the composition chosen, the particular disease, the weight, the physical condition, and the age of the mammal, and whether prevention or treatment is to be achieved. Such factors can be readily determined by the clinician employing animal models or other test systems which are well known to the art One or more suitable unit dosage forms having the therapeutic agent(s) of the invention, which, as discussed below, may optionally be formulated for sustained release (for example using microencapsulation, see WO 94/07529, and U.S. Pat. No. 4,962,091 the disclosures of which are incorporated by reference herein), can be administered by a variety of routes including parenteral, including by intravenous and intramuscular routes. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for administration, they may be combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents of the invention can be prepared by procedures known in the art using well known and readily available ingredients. The therapeutic agents of the invention can also be formulated as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions, such as phosphate buffered saline solutions pH 7.0-8.0.

The agents of this invention can be formulated and administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium Ethylenediaminetetraacetic acid (EDTA). In addition, parenteral solutions can contain preservatives such as benzalkonium chloride, methyl- or propyl-paraben and chlorobutanol. Suitable pharmaceutical carriers are described in Remington's Pharmaceutical Sciences, a standard reference text in this field.

The active ingredients of the invention may be formulated to be suspended in a pharmaceutically acceptable composition suitable for use in mammals and in particular, in humans. Such formulations include the use of adjuvants such as muramyl dipeptide derivatives (MDP) or analogs that are described in U.S. Pat. Nos. 4,082,735; 4,082,736; 4,101,536; 4,185,089; 4,235,771; and 4,406,890. Other adjuvants, which are useful, include alum (Pierce Chemical Co.), lipid A, trehalose dimycolate and dimethyldioctadecylammonium bromide (DDA), Freund's adjuvant, and IL-12. Other components may include a polyoxypropylene-polyoxyethylene block polymer (Pluronic®), a non-ionic surfactant, and a metabolizable oil such as squalene (U.S. Pat. No. 4,606,918).

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

Accordingly, the pharmaceutical composition of the present invention may be delivered via various routes and to various sites in a mammal body to achieve a particular effect (see, e.g., Rosenfeld et al., 1991; Rosenfeld et al., 1991a; Jaffe et al., supra; Berkner, supra). One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

The active ingredients of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and mammal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular host.

These methods described herein are by no means all-inclusive, and further methods to suit the specific application will be apparent to the ordinary skilled artisan. Moreover, the effective amount of the compositions can be further approximated through analogy to compounds known to exert the desired effect.

Determining Effectiveness of Therapy

In one aspect, the level of one or more circulating miRs in a biological sample of a patient is used to monitor the effectiveness of a treatment regimen. In some embodiments, the level of one or more miRs in a test sample obtained from a treated subject can be compared to the level from a reference sample obtained from that subject prior to initiation of a treatment. Clinical monitoring of treatment typically entails that each patient serve as his or her own baseline control. In some embodiments, test samples are obtained at multiple time points following administration of the treatment. In these embodiments, measurement of level of one or more miRs in the test samples provides an indication of the extent and duration of in vivo effect of the treatment.

Kits

The present invention also pertains to kits useful in the methods of the invention. Such kits comprise components useful in any of the methods described herein, including for example, hybridization probes or primers (e.g., labeled probes or primers), reagents for detection of labeled molecules, oligonucleotide arrays, restriction enzymes, antibodies, allele-specific oligonucleotides, means for amplification of a subject's nucleic acids, means for reverse transcribing a subject's RNA, means for analyzing a subject's nucleic acid sequence, and instructional materials. For example, in one embodiment, the kit comprises components useful for the detection and quantification of at least one miR associated with head or brain injury. In one embodiment, the kit comprises components for detecting the level or activity of one or more of the miRs associated with head or brain injury as elsewhere described herein.

The present invention also provides kits for diagnosing head or brain injury, comprising a probe for one or more nucleic acid markers known to be differentially expressed in head or brain injury. In one particular embodiment, the kit comprises reagents for quantitative amplification of the selected markers. Alternatively, the kit may comprise a microarray. In some embodiments the kit comprises 2 or more probes. In other embodiments, the kits may contain 3, 4, 5, 6, 7, 8, 9, 10, 15, 20, 25, or more probes.

In a further embodiment, the kit comprises the components of an assay for monitoring the effectiveness of a treatment administered to a subject in need thereof, containing instructional material and the components for determining whether the level of a marker of the invention in a biological sample obtained from the subject is modulated during or after administration of the treatment. In various embodiments, to determine whether the level of a marker of the invention is modulated in a biological sample obtained from the subject, the level of the marker is compared with the level of at least one comparator control contained in the kit, such as a positive control, a negative control, a historical control, a historical norm, or the level of another reference molecule in the biological sample. In certain embodiments, the ratio of the marker and a reference molecule is determined to aid in the monitoring of the treatment.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out exemplary embodiments of the present invention, and are not to be construed as limiting in any way the remainder of the disclosure.

Example 1: Exosomal microRNAs as Potential Biomarkers for Concussive and Subconcussive Head Impacts The purpose of this study was to identify a unique circulating exosomal microRNA profile indicative of subconcussive head impact. A common soccer heading task was used as a controlled head impact model to elicit subconcussive head impact in college males (n=6), in which subjects headed a soccer ball 10 times at a set velocity from ~30 meters away. Pre, immediately post, and 24 hours post blood sample were collected. Exosomes were isolated from plasma, and total RNA, including microRNA, was isolated from exosomes. Small RNA Next generation sequencing (NGS) was performed on microRNAs isolated from exosomes in pre and 24 hour post plasma to unbiasedly identify alterations in levels of exosomal microRNAs. A unique microRNA signature in circulating exosomes was identified 24 hours following subconcussive head impact. Specifically, based on abundance and fold change a small unique panel was identified including three microRNAs that were increased four fold or more (miR-92b-5p, miR-423-5p, and miR-24-3p), and four microRNAs that were decreased three fold or more (miR-7844-5p, miR-144-5p, miR-221-5p, and miR-22-3p).

To verify NGS results, quantitative real time polymerase chain reaction (qPCR) was performed on microRNAs at all time points. Further, to verify specificity of head impact exosomal microRNAs in the panel were measured via qPCR from a group the received soccer ball impact to the gastrocnemius muscle. Interestingly, several of the identified microRNAs are known to be involved in or associated with neurological dysfunction and disorders. In conclusion, subconcussive head impact leads to a unique circulating exosomal microRNAs signature that could potentially be indicative of head injury following repetitive subconcussive head impacts.

The Methods are Now Described

To characterize the exosomal microRNA changes in an unbiased way, small RNA Next generation sequencing (small RNA-Seq) was performed on microRNA samples isolated from plasma exosomes of subjects (n=3) from the same data set pre-heading and 24 hours after heading. Subsequent bioinformatics analysis was performed and identified a panel of seven microRNAs differentially expressed in exosomes 24 hours post head impact. While little to no current information exists on some of the identified microRNAs (ex. miR-92b-5p and miR-7844-5p), many of the identified microRNAs have been shown to be associated with neurological pathologies. While currently the similar expression patterns in the brain during pathological conditions and in the circulating exosomes following mild head injury is only correlative, it is feasible that the exosomal microRNA levels could be indicative or predictive of future neurological problems. Further, with little to no information in any area about miR-92b-5p and miR7884-5p these microRNAs could potentially be novel indicators of mild brain injury, and give insight into the pathology of subconcussive/concussive brain impact. Further, since it is clear from our unpublished data these microRNAs are known to change following head impact, altering the levels of the microRNAs to baseline levels could provide therapeutic benefit to people who receive head impact injury.

Example 2: miR-7844-5p as a Therapeutic for Concussive and Subconcussive Head Impacts Predictive modeling was performed to identify putative targets of those microRNAs that were identified as being biomarkers for subconcussive head impacts. The predictive modeling indicated that miR-7844-5p has a role in regulating multiple targets involved in head injury (FIG. 1).

miR-7844-5p was identified as being expressed in several tissues, with the greatest levels in brain, kidney and muscle (FIG. 2).

Figure 3:
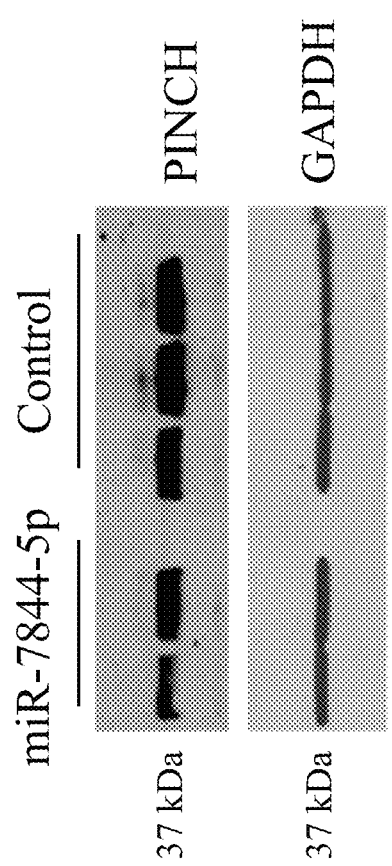
FIG. 3 depicts experimental results demonstrating that miR-7844-5p regulates PINCH1 protein.

Based on the predictions from the modeling, it was verified that miR-7844-5p functions to inhibit PINCH1 (LIMS1), a gene involved in growth factor receptor kinase signaling pathways (FIG. 3).

Based on the predictive modeling and the verification studies, miR-7844-5p has been identified as having therapeutic potential for the treatment of concussive and subconcussive head impacts.

What is claimed is:

1. A method of assessing the level of at least one micro RNA (miR) in a subject, wherein the subject has received a head impact, the method comprising:
   a) obtaining exosomal RNA from a biological sample from the subject, wherein the biological sample is selected from the group consisting of blood, serum, and a combination thereof, wherein the sample is obtained 24 hours post impact,
   b) contacting the sample with at least one selected from the group consisting of:
      i) at least one probe that hybridizes to at least miR selected from the group consisting of miR-7844-5p, miR-144-5p, miR-221-5p, miR-22-3p, -miR-92b-5p, and miR-423-5p, and
      ii) at least one primer for amplification of at least miR selected from the group consisting of miR-7844-5p, miR-144-5p, miR-221-5p, miR-22-3p, -miR-92b-5p, and miR-423-5p,
   c) determining the level of at least one miR selected from the group consisting of miR-7844-5p, miR-144-5p, miR-221-5p, miR-22-3p, -miR-92b-5p, and miR-423-5p in the biological sample,
   d) comparing the level of the at least one miR in the biological sample with the level of the at least one miRNA selected from the group consisting of miR-7844-5p, miR-144-5p, miR-221-5p, miR-22-3p, miR-92b-5p, and miR-423-5p in a comparator, wherein the comparator is the level of the miRNA in one or more healthy subject of reasonably matched background, and
   e) identifying the subject as having a substantial change in miR levels when the level of the at least one miRNA is at least one selected from the group consisting of a decreased level of miR-7844-5p, a decreased level of miR-144-5p, a decreased level of miR-221-5p, a decreased level of miR-22-3p, an increased level of miR-92b-5p, and an increased level of miR-423-5p,
   wherein the level of the at least one miRNA selected from the group consisting of miR-7844-5p, miR-144-5p, miR-221-5p, and miR-22-3p is lower than the level of the at least one miRNA in the comparator by at least three-fold;
   wherein the level of the at least one miRNA selected from the group consisting of miR-92b-5p and miR-423-5p is greater than the level of the at least one miRNA in the comparator by at least three-fold.

2. A method of identifying at least one dysregulated micro RNA (miR) in a subject, wherein the subject has received a head impact, the method comprising:
   a) obtaining exosomal RNA from a biological sample from the subject, wherein the biological sample is selected from the group consisting of blood, serum, and a combination thereof, wherein the sample is obtained prior to exposure to any head impact,
   b) obtaining exosomal RNA from a biological sample from the subject, wherein the biological sample is selected from the group consisting of blood, serum, and a combination thereof, wherein the sample is obtained 24 hours post impact,
   c) contacting the sample with at least one selected from the group consisting of:
      i) at least one probe that hybridizes to at least miR selected from the group consisting of miR-7844-5p, miR-144-5p, miR-221-5p, miR-22-3p, -miR-92b-5p, and miR-423-5p, and
      ii) at least one primer for amplification of at least miR selected from the group consisting of miR-7844-5p, miR-144-5p, miR-221-5p, miR-22-3p, -miR-92b-5p, and miR-423-5p,
   d) determining the level of at least one miR selected from the group consisting of miR-7844-5p, miR-144-5p, miR-221-5p, miR-22-3p, -miR-92b-5p, and miR-423-5p in the biological sample,
   e) comparing the level of the at least one miR in the biological sample with the level of the at least one miR selected from the group consisting of miR-7844-5p, miR-144-5p, miR-221-5p, miR-22-3p, miR-92b-5p, and miR-423-5p in a comparator, wherein the comparator is the level of the miR in one or more healthy subject of reasonably matched background, and
   f) identifying the miR as being dysregulated when the level of the at least one miR selected from the group consisting of miR-7844-5p, miR-144-5p, miR-221-5p, and miR-22-3p is at least three-fold lower than in the comparator and/or at least one miR selected from the group consisting of miR-92b-5p and miR-423-5p is at least four-fold greater than in the comparator.

* * * * *